United States Patent
Basu et al.

(10) Patent No.: US 11,904,310 B2
(45) Date of Patent: Feb. 20, 2024

(54) HIGH-THROUGHPUT DYNAMIC REAGENT DELIVERY SYSTEM

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US); DANA-FARBER CANCER INSTITUTE, INC., Boston, MA (US)

(72) Inventors: Anindita Basu, Cambridge, MA (US); Christopher B. Ford, Cambridge, MA (US); Aviv Regev, Cambridge, MA (US); David A. Weitz, Cambridge, MA (US); Asaf Rotem, Boston, MA (US); Kevin Struhl, Cambridge, MA (US)

(73) Assignees: The Broad Institute, Inc., Cambridge, MA (US); Massachusetts Institute of Technology, Cambridge, MA (US); President and Fellows of Harvard College, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 599 days.

(21) Appl. No.: 15/772,035

(22) PCT Filed: Oct. 28, 2016

(86) PCT No.: PCT/US2016/059600
§ 371 (c)(1),
(2) Date: Apr. 27, 2018

(87) PCT Pub. No.: WO2017/075549
PCT Pub. Date: May 4, 2017

(65) Prior Publication Data
US 2018/0311669 A1  Nov. 1, 2018

Related U.S. Application Data

(60) Provisional application No. 62/247,344, filed on Oct. 28, 2015.

(51) Int. Cl.
*B01L 3/00* (2006.01)
*C12M 3/06* (2006.01)
(Continued)

(52) U.S. Cl.
CPC ... *B01L 3/502715* (2013.01); *B01L 3/502746* (2013.01); *C12M 23/12* (2013.01);
(Continued)

(58) Field of Classification Search
None
See application file for complete search history.

(56) References Cited

U.S. PATENT DOCUMENTS

| 4,683,195 A | 7/1987 | Mullis et al. |
| 4,683,202 A | 7/1987 | Mullis et al. |

(Continued)

FOREIGN PATENT DOCUMENTS

| EP | 2047910 A2 | 4/2009 |
| KR | 1020100060471 A | 6/2010 |

(Continued)

OTHER PUBLICATIONS

Invitation to Pay Additional Fees For PCT International Application No. PCT/US2016/059600, dated Jan. 6, 2017, 2.

(Continued)

*Primary Examiner* — Lore R Jarrett
(74) *Attorney, Agent, or Firm* — F. Brent Nix, Esq.; Johnson, Marcou, Isaacs & Nix, LLC

(57) ABSTRACT

The present invention generally relates to a controlled fluidic device to develop spatially complex environments to (Continued)

enhance the rate of evolution in cell populations. The method further provides an enhanced understanding in the emergence, for example, drug resistance during cancer chemotherapy.

21 Claims, 23 Drawing Sheets

(51) Int. Cl.
    *G01N 33/50*     (2006.01)
    *C12Q 1/02*     (2006.01)
    *C12M 1/34*     (2006.01)
    *C12Q 1/18*     (2006.01)
    *C12M 1/32*     (2006.01)
    *B01L 3/02*     (2006.01)

(52) U.S. Cl.
    CPC .......... *C12M 23/16* (2013.01); *C12M 41/46* (2013.01); *C12Q 1/025* (2013.01); *C12Q 1/18* (2013.01); *G01N 33/502* (2013.01); *G01N 33/5008* (2013.01); *G01N 33/5011* (2013.01); *B01L 3/0241* (2013.01); *B01L 2200/027* (2013.01); *B01L 2200/10* (2013.01); *B01L 2300/08* (2013.01); *B01L 2300/0864* (2013.01); *B01L 2300/0867* (2013.01); *B01L 2400/086* (2013.01)

(56) References Cited

U.S. PATENT DOCUMENTS

| | | | |
|---|---|---|---|
| 5,589,352 A * | 12/1996 | Breznak | C12M 35/08 435/34 |
| 6,033,880 A | 3/2000 | Haff et al. | |
| 6,524,456 B1 | 2/2003 | Ramsey et al. | |
| 6,617,145 B2 | 9/2003 | Boone et al. | |
| 7,041,481 B2 | 5/2006 | Anderson et al. | |
| 7,129,091 B2 | 10/2006 | Ismagilov et al. | |
| 7,708,949 B2 | 5/2010 | Stone et al. | |
| RE41,780 E | 9/2010 | Anderson et al. | |
| 8,216,526 B2 | 7/2012 | Locascio et al. | |
| 8,273,573 B2 | 9/2012 | Ismagilov et al. | |
| 8,304,193 B2 | 11/2012 | Ismagilov et al. | |
| 8,329,407 B2 | 12/2012 | Ismagilov et al. | |
| 8,449,837 B2 | 5/2013 | Levchenko et al. | |
| 8,658,430 B2 | 2/2014 | Miller et al. | |
| 8,822,148 B2 | 9/2014 | Ismagliov | |
| 8,835,358 B2 | 9/2014 | Fodor et al. | |
| 8,889,083 B2 | 11/2014 | Ismagilov et al. | |
| 9,089,844 B2 | 7/2015 | Hiddessen et al. | |
| 9,126,160 B2 | 9/2015 | Ness et al. | |
| 9,216,392 B2 | 12/2015 | Hindson et al. | |
| 9,290,808 B2 | 3/2016 | Fodor et al. | |
| 9,290,809 B2 | 3/2016 | Fodor et al. | |
| 9,315,857 B2 | 4/2016 | Fu et al. | |
| 9,347,059 B2 | 5/2016 | Saxonov | |
| 9,388,465 B2 | 7/2016 | Hindson et al. | |
| 9,500,664 B2 | 11/2016 | Ness et al. | |
| 9,567,631 B2 | 2/2017 | Hindson et al. | |
| 9,567,645 B2 | 2/2017 | Fan et al. | |
| 9,567,646 B2 | 2/2017 | Fan et al. | |
| 9,598,736 B2 | 3/2017 | Fan et al. | |
| 9,636,682 B2 | 5/2017 | Hiddessen et al. | |
| 9,637,799 B2 | 5/2017 | Fan et al. | |
| 9,644,204 B2 | 5/2017 | Hindson et al. | |
| 9,649,635 B2 | 5/2017 | Hiddessen et al. | |
| 9,689,024 B2 | 6/2017 | Hindson et al. | |
| 9,695,468 B2 | 7/2017 | Hindson et al. | |
| 9,708,654 B2 | 7/2017 | Hunicke-Smith et al. | |
| 9,708,659 B2 | 7/2017 | Fodor et al. | |
| 9,816,121 B2 | 11/2017 | Agresti et al. | |
| 9,816,137 B2 | 11/2017 | Fodor et al. | |
| 9,826,137 B2 | 11/2017 | Yokomizo | |
| 9,845,502 B2 | 12/2017 | Fodor et al. | |
| 9,856,530 B2 | 1/2018 | Hindson et al. | |
| 9,885,034 B2 | 2/2018 | Saxonov | |
| 2002/0172965 A1 | 11/2002 | Kamb et al. | |
| 2005/0172476 A1 | 8/2005 | Stone et al. | |
| 2007/0015137 A1 | 1/2007 | Zantl et al. | |
| 2007/0195127 A1 | 8/2007 | Ahn et al. | |
| 2008/0003142 A1 | 1/2008 | Link et al. | |
| 2008/0014589 A1 | 1/2008 | Link et al. | |
| 2009/0042737 A1 | 2/2009 | Katz et al. | |
| 2009/0311737 A1 * | 12/2009 | Locascio | B01F 15/0404 435/29 |
| 2010/0002241 A1 | 1/2010 | Hirose | |
| 2010/0022414 A1 | 1/2010 | Link et al. | |
| 2010/0137163 A1 | 6/2010 | Link et al. | |
| 2010/0172803 A1 | 7/2010 | Stone et al. | |
| 2010/0234674 A1 | 9/2010 | Wheeler et al. | |
| 2011/0003372 A1 * | 1/2011 | Jeon | C12M 41/46 422/68.1 |
| 2011/0319298 A1 | 12/2011 | Benner et al. | |
| 2012/0122714 A1 | 5/2012 | Samuels et al. | |
| 2012/0219947 A1 | 8/2012 | Yurkovetsky et al. | |
| 2012/0220494 A1 | 8/2012 | Samuels et al. | |
| 2013/0274117 A1 | 10/2013 | Church et al. | |
| 2013/0316392 A1 | 11/2013 | Anant et al. | |
| 2014/0057311 A1 * | 2/2014 | Kamm | C12M 25/14 435/29 |
| 2014/0154703 A1 * | 6/2014 | Skelley | B01L 3/502761 435/7.23 |
| 2014/0155295 A1 | 6/2014 | Hindson et al. | |
| 2014/0235506 A1 | 8/2014 | Hindson et al. | |
| 2014/0357500 A1 | 12/2014 | Vigneault et al. | |
| 2015/0005199 A1 | 1/2015 | Hindson et al. | |
| 2015/0011430 A1 | 1/2015 | Saxonov | |
| 2016/0139110 A1 * | 5/2016 | Zantl | G01N 33/5029 435/287.1 |
| 2018/0030515 A1 | 2/2018 | Regev et al. | |

FOREIGN PATENT DOCUMENTS

| | | |
|---|---|---|
| WO | 9614746 A1 | 5/1996 |
| WO | 02099078 A2 | 12/2002 |
| WO | 2004002627 A2 | 1/2004 |
| WO | 2004016767 A2 | 2/2004 |
| WO | 2005003291 A2 | 1/2005 |
| WO | 2007089541 A2 | 8/2007 |
| WO | 2009036379 A2 | 3/2009 |
| WO | 2010024779 A1 | 3/2010 |
| WO | 2012050981 A1 | 4/2012 |
| WO | 2013188872 A1 | 12/2013 |
| WO | 2014026032 A2 | 2/2014 |
| WO | 2014047561 A1 | 3/2014 |
| WO | 2015032900 A1 | 3/2015 |
| WO | 2016040476 A1 | 3/2016 |
| WO | 2017/075549 A1 | 5/2017 |

OTHER PUBLICATIONS

International Search Report and Written Opinion issued in International Application No. PCT/US2016/059600, dated Mar. 17, 2017.
Zhang, et al., "Acceleration of Emergence of Bacterial Antibiotic Resistance in Connected Microenvironments", Science, vol. 3333, Sep. 23, 2011, 5 pages.
"2017 Top 10 Innovations", 2017 Top 10 Innovations, The Scientist, pp. 1-11, Dec. 1, 2017.
"Acrylamide Product Information Sheet", Sigma Aldrich 1996 Product Information Sheet, A8887, pp. 1-2, 1996.
"American Cell Biology Meeting Program 2017", The 2017 ASCB EMBO Meeting, pp. 1-198, Dec. 2017.
"An Introduction to Linked-Read Technology for a More Comprehensive Genome and Exome Analysis", 10X Genomics Technical Note, pp. 1-5, 2016.
Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.

(56) References Cited

OTHER PUBLICATIONS

"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.
"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG000184 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | Rev C, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell A Chip Kit, 16 rxns PN-1000009, 10X Genomics, pp. 1-74, CG00052 | Rev E, 2018.
"Chromium Single Cell 3' Reagent Kits v2 Safety Data Sheets, Chromium Single Cell A Chip Kit, 48 runs", 10X Genomics, PN-120236, Oct. 6, 2016.
"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"DdSEQ™ Cartridge Holder", Bio-Rad ddSEQ™ Cartridge Holder #12004739, 2016.
"DdSEQ™ Single-Cell Isolator—Accessories", ddSEQ™ Single-Cell Isolator—Accessories—Bio-Rad, pp. 1-2, 2016.
"DdSEQ™ Single-Cell Isolator—Ordering", ddSEQ™ Single-Cell Isolator Bio-Rad, 2016.
"DdSEQ™ Single-Cell Isolator by Bio-Rad", Bio-Rad, pp. 1-8, Select Science, 2019.
"DdSEQ™ Single-Cell Isolator by Bio-Rad", ddSEQ™ Single-Cell Isolator, Bio-Rad, pp. 1-2, 2016.
"DdSEQ™ Test Cartridges", Bio-Rad ddSEQ™ Test Cartridges #12003862, 2016.
"Deoxyribonuclease I from bovine pancreas", Sigma-Aldrich Deoxyribonuclease I from bovine pancreas, CAS No. 9003-98-9, 2018.
"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 dated Apr. 17, 2018, 4 pages.
Office Action issued by the European Patent Office in Application No. 15767655.2 dated Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases-Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document # 1000000021454 v00, pp. 1-6, Feb. 2017.
"Illumina® | Bio-Rad® Single Cell Sequencing", illumina | Bio-Rad, pp. 1-37, 2015.
"Illumina® Bio-Rad® SureCellTM WTA 3' Library Prep Kit for the ddSEQTM System", illumina | Bio-Rad, pp. 1-4, 2015.
"Infoporte—Cores", Infoporte | Version: 7.1.1 | © 2019 The University of North Carolina at Chapel Hill.
"The Instrument—Chromium Controller Compatible Solutions", 10X Genomics, pp. 1-7, 2019.
The Broad Institute, Inc., et al., "Communication pursuant to Article 94(3) EPC for EP 168610160.0", dated Apr. 1, 2020, 5 pages.
The Broad Institute, Inc., et al., "Extended European Search Report for EP 168610160.0", dated Jul. 16, 2019, 11 pages.
"Markman Order In re Certain Microfluidic Systems and Components Thereof and Products Containing Same", Docket Alarm, pp. 1-6, Oct. 31, 2018.
"Molecular and Genomics Core Facility Equipment", Molecular and Genomics Core Facility, pp. 1-7, 2018.
"N,N'-Methylenebis(acrylamide)", 146072 Sigma-Aldrich, CAS No. 110-26-9, 2018.
"Neuroscience 2017 Program", Society for Neuroscience, pp. 1-2, 2017.
"Notice of Intent to Certify Sole Source", Sole Source Certification No. SS5098 for Bio-Rad ddSeq Single Cell Isolation System and associated accessories, pp. 1-5, Jun. 5, 2017.
"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.
"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.
"Reverse Transcription Reaction Setup—Seven Important Considerations", ThermoFisher Scientific, pp. 1-15, 2018.

(56) References Cited

OTHER PUBLICATIONS

"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCellTM RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell WTA 3' Library Prep Kit Support, Questions & Answers", Illumina, pp. 1-4, 2019.
"SureCell WTA 3' Library Prep Kit for the ddSEQ System", Ilumina, pp. 1-6, 2019.
"The Illumina Bio-Rad Single Cell Sequencing Solution", illumina | Bio-Rad, pp. 1-3, 2018.
"The Illumina Bio-Rad Single-Cell Sequencing Solution Robust and scalable single-cell sequencing", illumina | Bio-Rad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, dated Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178, dated Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.
International Preliminary Report on Patentability issues in International Application No. PCT/US2015/049178, dated Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.
Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.
Berman, et al., "Mapping the Stereotyped Behaviour of Free Moving Fruit Flies", Journal of the Royal Society Interface, vol. 11, Issue 99, 20140672, pp. 1-12, Aug. 20, 2014.

Binladen, et al., "The Use of Coded PCR Primers Enables High-Throughput Sequencing of Multiple Homolog Amplification Products by 454 Parallel Sequencing", PLoS One; vol. 2, Issue 2: e197, pp. 1-9, Feb. 14, 2007.
Bitinaite, et al., "User™ friendly DNA engineering and cloning method by uracil excision", Nucleic Acids Res., vol. 35, No. 6, pp. 1992-2002, Publised online Mar. 6, 2007.
Black, Chris, "The ChromiumTM System: Linked Read And Single Cell RNA-Seq Applications Powered By GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of The Royal Society A Mathematical Physical and Engineering Sciences, vol. 362, Issue 1818, pp. 1087-1104, Jun. 2004.
Britten, et al., "Repeated Sequences in DNA. Hundreds of Thousands of Copies of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
Rothberg, et al., "An integrated semiconductor device enabling non-optical genome sequencing", Nature, vol. 475, pp. 348-352, Jul. 21, 2011.
Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.
Song, et al., "A Microfluidic System for Controlling Reaction Networks in Time", Angew. Chem. Int. Ed. 2003, vol. 42, No. 7, pp. 767-772, ,Received: Sep. 6, 2002.
Soumillon, et al., "Characterization of Directed Differentiation by High-Throughput Single-Cell RNA-Seq", BioRxiv, pp. 1-13, Preprint: Mar. 5, 2014.
Spies, et al., "Genome-wide reconstruction of complex structural variants using read clouds", Nat Methods, vol. 14, No. 9, pp. 915-920, Sep. 2017.
Stoeckius, et al., "Large-scale simultaneous measurement of epitopes and transcriptomes in single cells", Nature Methods, vol. 14, No. 9, pp. 865-868, Sep. 2017.
Taylor, et al., "A scalable high-throughput method for RNA-Seq analysis of thousands of single cells", illumina | Bio-Rad, 2016.
Tewhey, et al., "Microdroplet-based PCR enrichment for large-scale targeted sequencing", Nature Biotechnology, vol. 27, No. 11, pp. 1025-1031, Nov. 1, 2009.
The Broad Institute, Inc., "Communication Pursuant to Rule 164(2)(b) and Article 94(3) EPC", dated Jul. 11, 2018, 12 pages.
Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.
Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.
Wu, et al., "Termination of DNA synthesis by N6-alkylated, not 3'-O-alkylated, photocleavable 2'-deoxyadenosine triphosphates", Nucleic Acids Res., vol. 35, No. 19, pp. 6339-6349, Sep. 18, 2007.
Yan, et al., "Intestinal enteroendocrine lineage cells possess homeostatic and injury-inducible stem cell activity", Cell Stem Cell, vol. 21, No. 1, pp. 78-90, Jul. 6, 2017.

(56) References Cited

OTHER PUBLICATIONS

Yan, et al., "Non-equivalence of Wnt and R-spondin ligands during Lgr5+ intestinal stem cell self-renewal", Nature, vol. 545, No. 7653, pp. 238-242, May 11, 2017.
Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.
Zheng, et al., "Massively parallel digital transcriptional profiling of single cells", Nature Communications, vol. 8, Article No. 14049, pp. 1-12, Published: Jan. 16, 2017.
Metzker, "Sequencing technologies—the next generation", Nature Reviews, Genetics, vol. 11, pp. 31-46, Published online: Dec. 8, 2009.
"International Preliminary Report on Patentability_for_PCT_Application_No_PCT_US2016_059600", dated May 11, 2018.
Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, pp. 12069-12074, Jul. 17, 2007.
Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Ding, et al., "Progress Towards a Systematic Comparison of Single Cell RNA-Seq Methods", Broad Institute, Feb. 12, 2019.
Dixit, et al., "Perturb-Seq: Dissecting Molecular Circuits with Scalable Single-Cell RNA Profiling of Pooled Genetic Screens", Cell, vol. 167, Issue 7, pp. 1853-1866, Dec. 15, 2016.
Dobin, et al., "STAR: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.
Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317, Received: May 18, 2000.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pates 1-17, 2017.
Gueroult, et al., "How Cations Can Assist DNase I in DNA Binding and Hydrolysis", PLoS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, , vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.
Kovall, et al., "Structural, functional, and evolutionary relationships between exonuclease and the type II restriction endonucleases", Proc Natl Acad Sci U S A., vol. 95, No. 14, pp. 7893-7897, Jul. 1998.
Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.
Kutnjak, et al., "Calorimetric study of octylcyanobiphenyl liquid crystal confined to a controlled-pore glass.", Physical Review E, The American Physical Society, pp. 021705-1-021705-12, Published: Aug. 22, 2003.
Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.
Macosko, et al., "Highly Parallel Genome-Wide Expression Profiling of Individual Cells Using Nanoliter Droplets", Cell, vol. 161, No. 5, pp. 1202-1214, May 21, 2015.
Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.
Margulies, et al., "Genome Sequencing in Open Microfabricated High Density Picoliter Reactors", Nature, vol. 437, No. 7057, pp. 376-380, Sep. 15, 2005.
McKenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.
Metzker, "Emerging technologies in DNA sequencing.", Genome Res., vol. 15, No. 12, pp. 1767-1776, Dec. 2005.
Miller, et al., "Basic Concepts of Microarrays and Potential Applications in Clinical Microbiology", Clinical Microbiology Reviews, vol. 22, No. 4, pp. 611-633, Oct. 2009.
Mol, et al., "DNA-bound structures and mutants reveal abasic DNA binding by APE1 and DNA repair coordination.", Nature, vol. 403, No. 6768, pp. 451-456, Jan. 27, 2000.
Narasimhan, et al., "Health and population effects of rare gene knockouts in adult humans with related parents", Science, vol. 352, No. 6284, pp. 474-477, Apr. 22, 2016.
Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.

(56) References Cited

OTHER PUBLICATIONS

Novak, et al., "Single cell multiplex gene detection and sequencing with microfluidically generated agarose emulsions", Angew. Chem. Int. Ed., pp. 1-11, 2010.
Novak, et al., "Single Cell Multiplex Gene Detection and Sequencing with Microfluidically Generated Agarose Emulsions", Agnew. Chem. Int. Ed., pp. 390-395, Jan. 10, 2011.
Pal, et al., "Construction of developmental lineage relationships in the mouse mammary gland by single-cell RNA profiling", Nature Communications, vol. 8, Article No. 1627, pp. 1-14, Nov. 20, 2017.
Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.
Pennisi, "Development Cell by Cell", Science, vol. 362, Issue 6421, pp. 1344-1345, Dec. 21, 2018.
Perona, "Type II restriction endonucleases.", Methods, vol. 28, No. 3, pp. 353-364, Accepted: Jul. 30, 2002.
Peterson, et al., "The effect of surface probe density on DNA hybridization", Nucleic Acids Res., vol. 29, No. 24, pp. 5163-5168, Dec. 15, 2001.
Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.

Final Office Action for U.S. Appl. No. 15/453,405, issued by the U.S. Patent Office dated Mar. 27, 2019, 17 pages.
Park, et al., "Simultaneous Generation of Chemical Concentration and Mechanical Shear Street Gradients Using Microfluidic Osmotic Flow Comparable to Interstitial Flow", Lab on a Chip, vol. 9. No. 15, 2009, 2194-2202.
The Broad Institute Inc., et al., "Supplementary Partial European Search Report for EP 16861016", dated Apr. 15, 2019, 14 pages.
Turner-Yovanovitch, et al., "Hexagonal-Chambered Microfluidic Device: A New Method and Device for Capturing and Culturing Environmental Microbes", www.cdn.vanderbilt.edu/vu-wp0/wp-content/uploads/sites/16/2015/08/27122712/Turner-Yovanovitch.pdf, Aug. 25, 2015, 3 pages.
Yang, et al., "Generation of Concentration Gradient by Controlled Flow Distribution and Diffusive Mixing in a Microfluidic Chip", Lap on a Chip, Royal Society of Chemistry, vol. 2, No. 3, Jan. 2002, pp. 158-163.
Klein, et al., "Droplet Barcoding for Single-Cell Transcriptomics Applied to Embryonic Stem Cells", Cell, vol. 161, No. 6, May 21, 2015, 1187-1201.
McDonald, et al., "Fabrication of Microfluidic Systems in Poly(dimethylsiloxane)", Electrophoresis, vol. 21, Issue 1, Jan. 2000, 27-40.
Ryan, et al., "Single-Cell Assays", Biomicrofluidics, vol. 5, No. 021501, 2011, 9 pages.

\* cited by examiner

HIGH-THROUGHPUT DYNAMIC REAGENT DELIVERY SYSTEM

CROSS-REFERENCE TO RELATED APPLICATIONS

This application is the U.S. National Stage of International Application No. PCT/US2016/059600, filed Oct. 28, 2016, which claims the benefit of U.S. Provisional Patent Application No. 62/247,344, filed Oct. 28, 2015. The entire contents of the above-identified priority applications are hereby fully incorporated herein by reference.

FEDERAL FUNDING LEGEND

This invention was made with government support under Grant No. HG006193 awarded by the National Institutes of Health. The government has certain rights in the invention.

FIELD OF THE INVENTION

The present invention generally relates to a controlled fluidic device to develop spatially complex environments to enhance the rate of evolution in cell populations. The method further provides an enhanced understanding in the emergence, for example, drug resistance during cancer chemotherapy.

BACKGROUND OF THE INVENTION

The invention of the present application relates to developing spatially complex environments to enhance the rate of evolution in cell populations. Stress gradients, such as a temperature or concentration of a fluid, imposed on a connected network of populations allows the relative fitness of a mutant which acquires some resistance to the local stress to join a population exposed to even higher stress.

Performing studies that require data resolution at the single cell (or single molecule) level can be challenging or cost prohibitive under the best circumstances. Although techniques or instruments for single molecule or single cell analysis exist (e.g., digital polymerase chain reactions (PCR) or Fluidigm␣C1, respectively), none currently allow a scalable method for dynamically delivering reagents and/or appending molecular "information" to individual reactions such that a large population of reactions/assays can be processed and analyzed en masse while still maintaining the ability to partition results by individual reactions/assays.

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 108 samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Citation or identification of any document in this application is not an admission that such document is available as prior art to the present invention.

SUMMARY OF THE INVENTION

The invention of the present application relates to developing spatially complex environments to enhance the rate of evolution in cell populations. Stress gradients, such as a temperature or concentration of a fluid, imposed on a connected network of populations allows the relative fitness of a mutant which acquires some resistance to the local stress to join a population exposed to even higher stress.

The invention provides a controlled fluidic device for establishing a gradient, particularly a concentration gradient, comprising a closed chamber comprising one or more inlet port(s) that deliver two or more different fluids via separate inlet channels and at least one outlet port wherein the location of the one or more inlet port(s) and the at least one outlet port are located so that the flow of fluids can be controlled within the closed chamber and a gradient of the mixture of the two or more fluids from the two or more inlet ports is established.

In an embodiment of the invention, the peripheral flow can be established such that the inlet and outlet can be on the same side of any given fluid with two pairs of separate fluid inlet/outlet ports while concurrently occurring in the same plane with a moveable gradient or interface.

In an embodiment of the invention, the controlled fluid device further comprises a plurality of wells, the wells in fluid communication with the inlet ports such that the concentration of the mixture of the two more fluids of each respective well is related to the location of the respective well with respect to the inlet ports.

In another embodiment of the invention, the controlled fluidic device further comprises a fluid channel extending between a first said wells and a second of said wells such that the first of said wells is in fluid communication with the second of said wells.

In an embodiment of the invention, one of the two or more fluids is a null solution for forming a concentration gradient of another of the two or more fluids. In another embodiment, one of the two or more fluids may include a substance for which a concentration gradient is formed. In a further embodiment of the invention, the controlled fluid device comprises a substance which is capable of being dissolved in one of the two or more fluids. In another embodiment, the substance is capable of being homogenously carried in one of the two or more fluids. In an embodiment, the controlled fluidic device comprises a closed chamber, inlet port, outlet port, and inlet channels which are sized to accept magnetic beads. In an embodiment of the invention, the controlled fluidic device comprises a substance which is a chemical or a drug.

In a related aspect, the invention provides a controlled fluidic device wherein the controlled fluidic device is a polygonal plate having an upper surface and a lower surface and a peripheral plate edge having a pre-determined depth. In an embodiment of the invention, the controlled fluidic device comprises a device wherein at least one of the two fluids includes at least one component for which a gradient could be established. In an another embodiment, the at least one component is a drug. In a further embodiment, the controlled fluidic device further comprises another component for which a concentration could be established. In an embodiment, the controlled fluidic device comprises a drug. In another embodiment, the another component is a drug.

In a related aspect, the invention provides a controlled fluidic device comprising at least component which includes at least two subcomponents. In an embodiment of the invention, the controlled fluidic device comprises a closed chamber comprising a chip. In an embodiment of the invention, the controlled fluidic device comprises a polygonal plate. In an embodiment of the invention, the polygonal plate are separated by approximately 1.45 mm. In an embodiment of the invention, the polygonal plate are separated by approximately 1.65 mm. In an embodiment of the invention, the polygonal plate are separated by approximately 1.40 mm. In an embodiment of the invention, the polygonal plate is a hexagonal plate. In an embodiment of the invention, the polygonal plate is a rectangular plate.

In an embodiment of the invention, the controlled fluidic device comprises at least one peripheral flow channel which is defined by laminar flow at least one of the fluids in the closed chamber. In an embodiment of the invention, the controlled fluidic device comprises a first of said inlet ports for a first of said different fluids which is adjacent to an outlet port for a second of said different fluids.

The invention provides a method of identifying altered chemical resistance in a bacterial population in the controlled fluidic device as described above, the method comprising: synthesizing a mutant bacterial strain to express fluorescent proteins; introducing a known concentration of the bacterial strain into the closed chamber; administering the two or more different fluids into the closed chamber via the two more inlet ports; isolating DNA from a single cell; purifying DNA from bacteria; sequencing DNA from bacteria; preparing and sequencing a single composite sequence library; wherein identification of alteration in level of expression compared to a baseline gene expression measurement of at least one biomarker is indicative of chemical resistance, and wherein the baseline gene expression measurement is the gene expression measured in the microfluidic well prior to administration of the two or more different fluids.

The present invention also provides a method of evaluating response in a cell population in the controlled fluidic device as described, the method comprising: introducing a cell population into the closed chamber; administering the two or more different fluids into the closed chamber via the two more inlet ports such that a concentration gradient is established in the closed chamber; and, measuring the response of the cell population at various concentrations across the concentration gradient.

In another aspect, the invention provides a method of identifying altered bacterial populations according to the method of evaluating a response, the method comprising: a microfluidic device having a closed chamber having an upper surface and a lower surface and a peripheral plate edge having a predetermined depth; a plurality of microfluidic wells extending from the upper surface of the closed chamber, each well connected to adjacent ones of the plurality of wells by microchannels extending from the upper surface of the plate and extending from a first well to a second well such that the first well is in fluid communication with the second well; wherein the microfluidic device and plurality of wells connected by microchannels creates a chemical concentration gradient in adjacent microfluidic wells wherein one microfluidic well has a different chemical concentration than an adjacent microfluidic well; providing a chemical dye via an inlet port of the closed chamber, wherein a first inlet provides a diluent and a second inlet provides a chemical of interest; providing a chemical via an inlet port of the closed chamber; optionally providing a second chemical via an inlet port of the closed chamber; an outlet port of the closed chamber; and, a peripheral flow channel adjacent a portion of the peripheral plate edge and extending from the inlet port to the outlet port.

In an embodiment, the method comprises a measurement of gene expression which is made by detecting the quantity of RNA transcribed by the biomarker. In another embodiment, the measurement of gene expression is made by detecting the quantity of DNA produced from reverse transcription of an RNA transcribed by the biomarker. In another embodiment, the measurement of gene expression is made by detecting a polypeptide or protein encoded by the biomarker. In a further embodiment, the at least one biomarker is operably linked to a fluorescent protein.

The present invention provides a method of identifying a compound associated with an altered bacterial population as described above, the method comprising: designing a combinatorial library wherein each member of the library comprises at least one pharmacophore associated with the altered gene expression; wherein alteration in level of expression compared to a baseline gene expression measurement of at least one biomarker is indicative of an altered bacterial population; synthesizing a plurality of compounds from said combinatorial library; and, screening said compounds for candidates associated with the altered bacterial population.

In an embodiment of the invention, the method comprises a closed chamber, wherein the closed chamber is a polygonal plate. In another embodiment, the method comprises microfluidic wells, wherein the microfluidic wells have a polygonal cross section in a plane parallel to the lower surface of the closed chamber, each well having a plurality of vertices, wherein the microchannels extending from the first well to the second well extend from a vertex of the polygonal cross section of the first well to a vertex of the polygonal cross section of the second well. In a further embodiment, the method comprises a peripheral flow channel, wherein the peripheral flow channel is defined by laminar flow of at least one of the fluids in the closed chamber.

The invention provides an array of controlled microfluidic devices, comprising a plurality of controlled microfluidic devices according to the controlled fluidic device for establishing a gradient, comprising a closed chamber comprising one or more inlet port(s) that deliver two or more different fluids via separate inlet channels and at least one outlet port wherein the location of the one or more inlet port(s) and the at least one outlet port are located so that the flow of fluids can be controlled within the closed chamber and a gradient of the mixture of the two or more fluids from the two or more inlet ports is established.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art up on consideration of the following detailed description of illustrated example embodiments.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
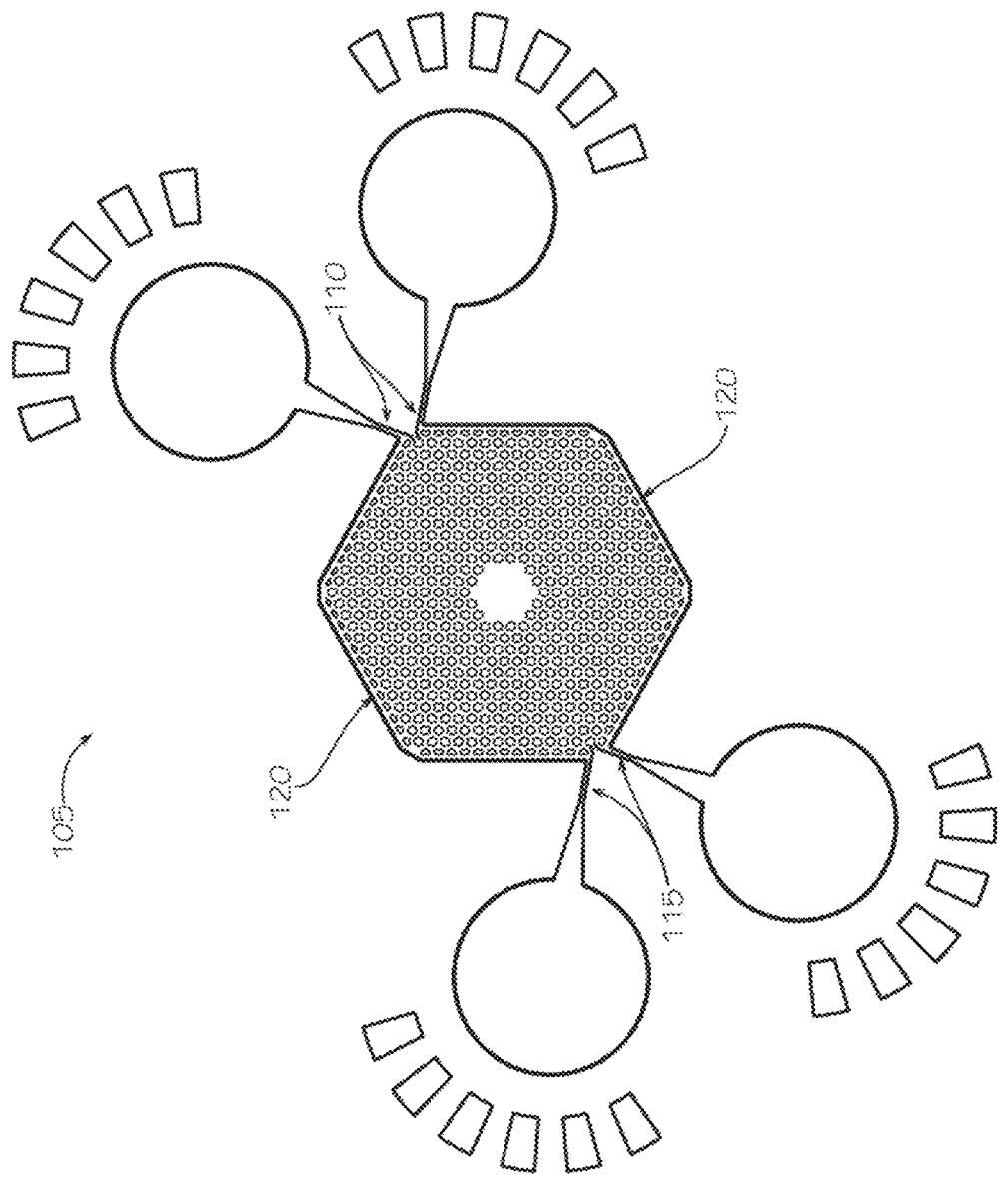
FIG. 1 illustrates an embodiment of a controlled fluidic device.

The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

The invention provides controlled fluidic devices, including microfluidic devices, and components thereof for establishing one or more gradients on the device, particularly one or more concentration gradients. In one aspect, a gradient chamber is used to define a gradient within the chamber. The gradient chamber may comprise a set of columns and depressed regions or wells which are configured to facilitate formation of a concentration gradient within the chamber. In another aspect, a set of stacked resistor lines may be used to mix two or more solutions to generate different concentrations of a given composition. In certain example embodiments, the resistor lines may feed into one or more droplet modules that generate a set of droplets wherein the droplets comprise varying concentrations of a target final solution to be screened. The droplets may further encapsulate reporter elements and/or cells, or the droplets may further be merged with a second set of droplets comprising reporter elements and/or cells.

In yet another aspect, the stacked resistor lines and gradient chamber may be used in conjunction on the same device, wherein the stacked resistor lines create different starting concentrations of a given compositions which are then flowed onto a gradient chamber to facilitate formation of a different concentration gradient on each device. Thus, the embodiments disclosed herein include devices comprising one or more stacked resistor lines, with or without droplet modules, one or more gradient chambers, or a combination thereof.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. Suitable materials for fabricating the microfluidic devices include, but are not limited to, polyacrylamide, polyethylene glycol, acrylonitrile, halogen bearing polymers, polyvinyl acetate, acrylic elastomers, polystyrene, polyimides, polyamides, polyurethanes, polysilanes, cyclic olefin copolymer (COC), polycarbonate, poly(dimethylsiloxane) (PDMS), and poly(methylacrylate) (PMMA). In one embodiment, soft lithography in PDMS may be used to prepare the microfluidic devices. For example, a mold may be made using photolithography which defines the location of flow channels, valves, and filters within a substrate. The substrate material is poured into a mold and allowed to set to create a stamp. The stamp is then sealed to a solid support, such as but not limited to, glass. In certain example embodiments, the devices and components thereof described herein may be fabricated using 3D printing.

Referring now to FIG. 1, in one example embodiment, the device may comprise one or more gradient chambers 105. A gradient chamber 105 may comprises one or more inlets 110 and one or more outlets 115. It should be understood that the arrangement and orientation of the inlets 110 and outlets 115 in FIG. 1 is illustrative only and that other configurations of inlets and outlets around the gradient chamber 115 are within the scope of the invention. For example, the orientation of the inlets 110 and outlets 115 may be reversed. In addition, in certain example embodiment, an inlet 110 and outlet 115 may be arranged on the same side of the chamber. See FIG. 4. The interior of the chamber 105 will be described in more detail with reference to FIGS. 2 and 3 below. In certain example embodiments the inlets 110 and outlets 115 may be located at or proximate to a vertex of the gradient chamber 105.

Figure 5A:
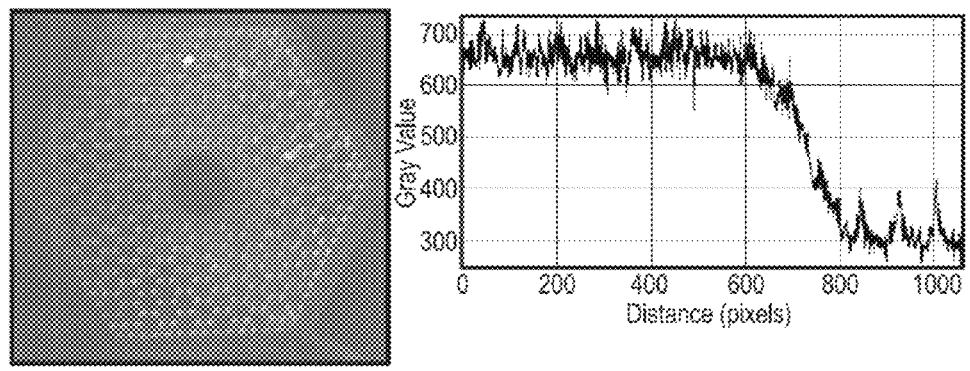
FIG. 5A illustrates PBS and rhodamine in PBS at one relative flow rate.
Figure 5B:
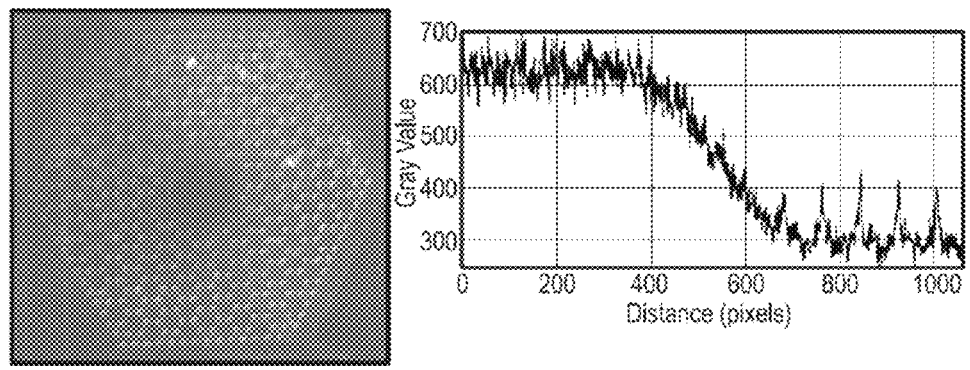
FIG. 5B illustrates PBS and rhodamine in PBS at a different relative flow rate.
Figure 5C:
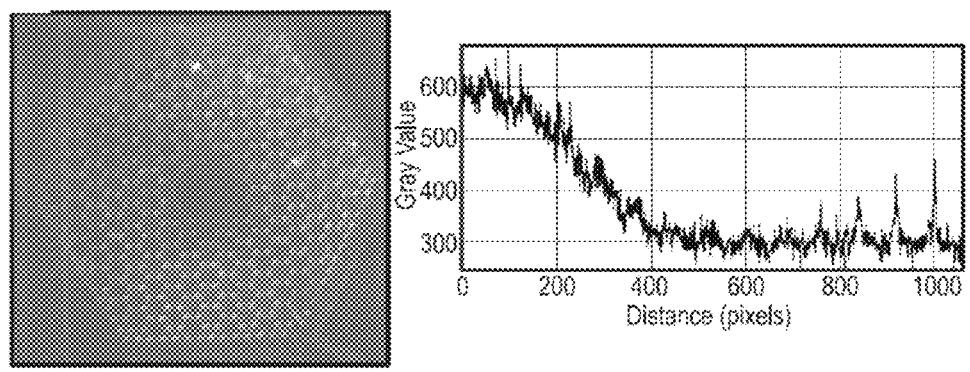
FIG. 5C illustrates PBS and rhodamine in PBS at another different relative flow rate.

The inlet 110 and outlets 115 may be further connected to valves, tubes, channels, additional chambers, syringes and/or pumps or the introduction and extraction of fluids into and from the chamber 105. The chamber 105 may be connected to fluid flow actuators that allow directional movement of fluids within the chamber 105 or a larger microfluidic device of which the chamber 105 is but a component. Example actuators include, but are not limited to, syringe pumps, mechanically actuated recirculating pumps, electroosmotic pumps, bulbs, bellows, diaphragms, or bubbles intended to force movement of fluids. The chamber 105 further comprises one or more peripheral channels 120 of a defined depth and oriented along all or portion of the outer edges of the chamber 105. In certain example embodiments, the peripheral channels 120 may connect an inlet 110 to an outlet 115. In certain example embodiments, the flow channel has a depth of approximately 5 μm to 500 μm and a width of approximately 5 μm to 500 μm. The peripheral channel may further comprise a series of openings 125 along an interior wall of the chamber that allow fluid communication with the interior space of the chamber 105. Example openings 125 may be more clearly seen in the inset of FIG. 3. The flow rate of the two solutions onto the gradient chamber will determine the concentration gradient formed. This is demonstrated in FIGS. 5A-5C, which shows a concentration gradient formed between a fluorescent dye solution and a carrier solution at different flow rates for each solution.

In certain example embodiments, the Reynolds number of the inlet 110 is low, for example less than about 1. In a further embodiment, the formula varies with the cross-section of the channel. In another embodiment, the channels have a rectangular/square cross-section. In a further embodiment, the channels have a circular cross-section. In another embodiment, one of the inlet ports and one of the outlet ports are located on opposite sides of the closed chamber. In certain example embodiments, the angle of separation is between 130 to 220 degrees. In one example embodiment, the angle of separation is between 150 to 210 degrees.

The shape of the gradient chamber may vary. The gradient chamber may be polygonal in shape. In certain example embodiments, the gradient chamber may be square-shaped, rectangular-shaped, or hexagonal. In one example embodiment, the gradient chamber is square-shaped. In another example embodiment, the gradient chamber is hexagonal shape. The size of the gradient chamber may be between 0.05 mm and 5 mm in length. In certain example embodiments, the gradient chamber is between 1 mm and 2 mm in length. The height of the chamber may be between 50 μM and 500 μM. In certain example embodiments, the gradient chamber is one-sided. In certain other example embodiments, the chamber is double-sided with separate chambers arranged on opposing sides. In certain example embodiments, the peripheral channels 120 may be between 0.05 mm and 0.5 mm wide and have a height of between 10 μm and 500 μm. The number of openings 125 in the peripheral channel may vary based on the length of the peripheral channel and the desired flow rate of fluid from the peripheral channel into the interior of the chamber 105. The flow rate interior of the chamber may be adjusted by adjusting the number of openings to increase the flow rate or decreasing the number of openings to decrease the flow rate.

Figure 2:
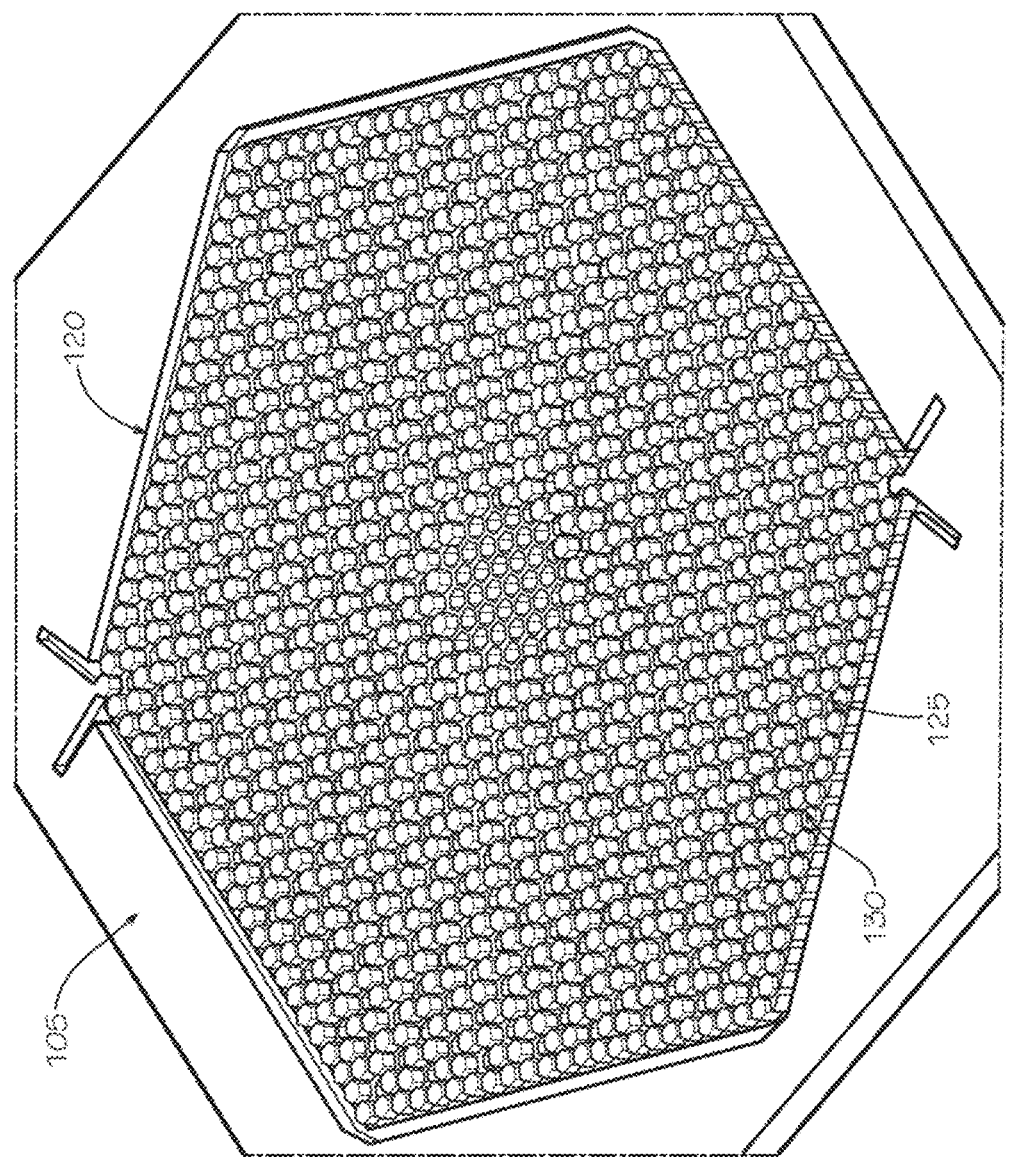
FIG. 2 is a diagram of an interior space of a chamber in accordance with certain example embodiments.
Figure 6A:
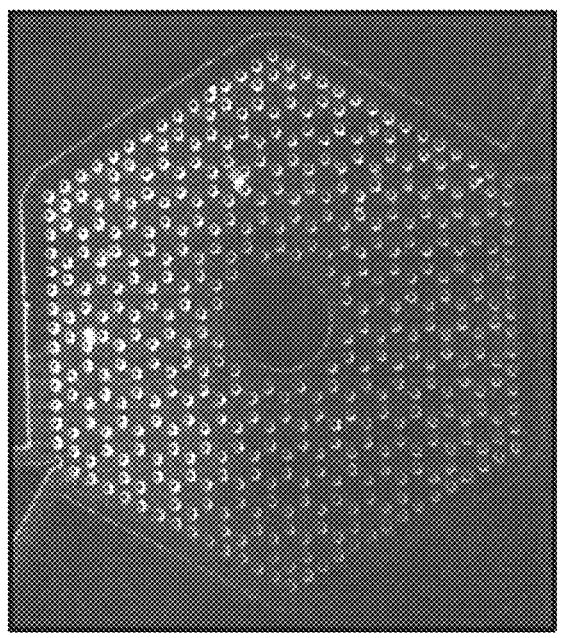
FIG. 6A illustrates another example of PBS and rhodamine in PBS at one relative flow rate.
Figure 6B:
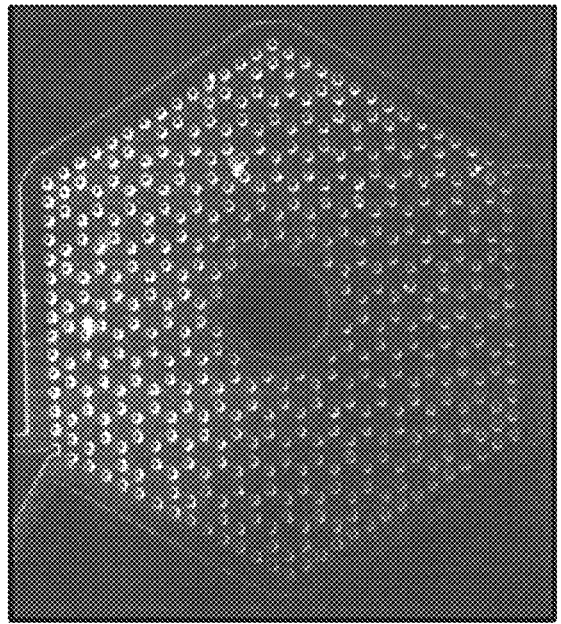
FIG. 6B illustrates another example of PBS and rhodamine in PBS at a different relative flow rate.
Figure 7:
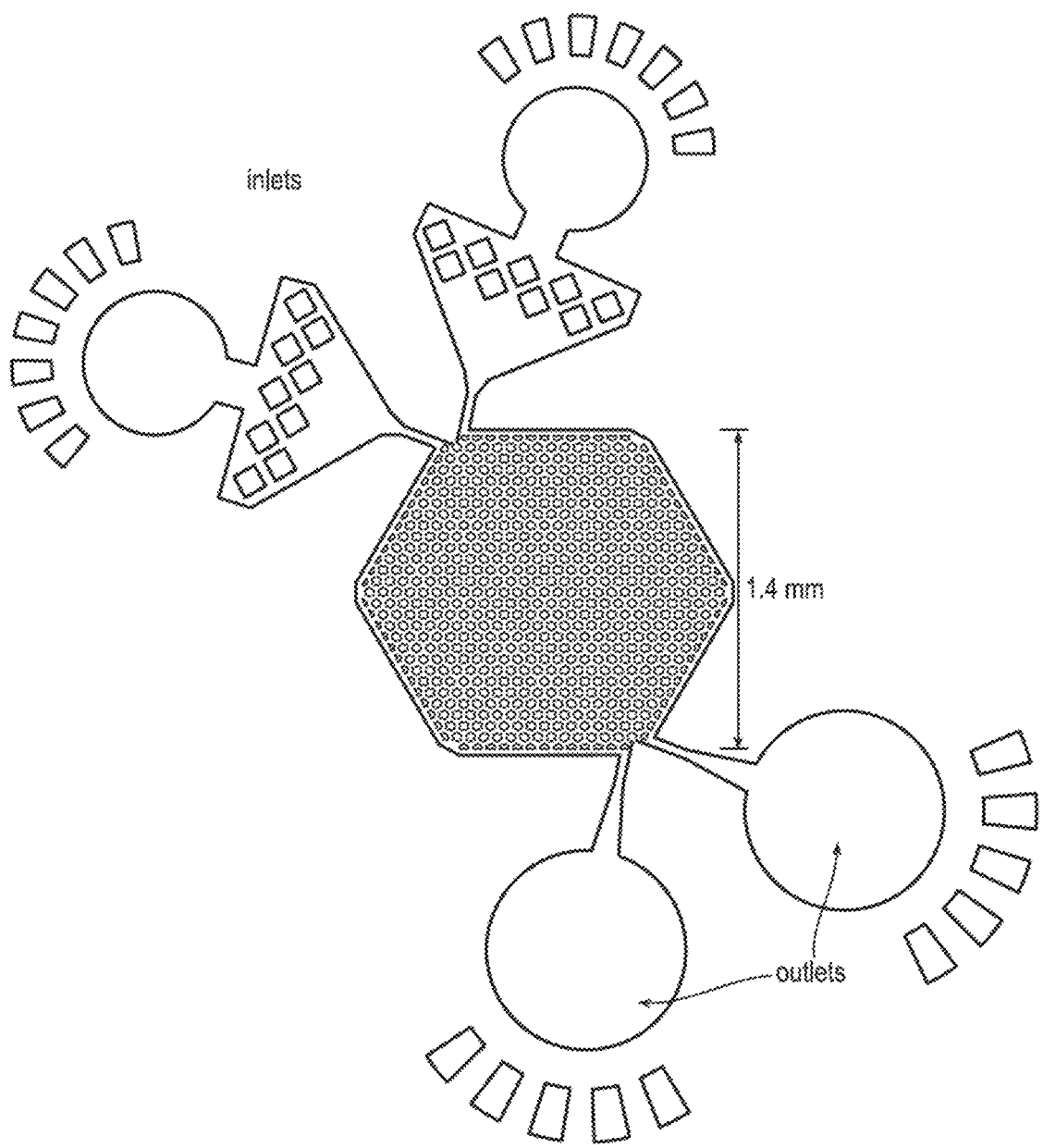
FIG. 7 illustrates a controlled fluidic device design.
Figure 8:
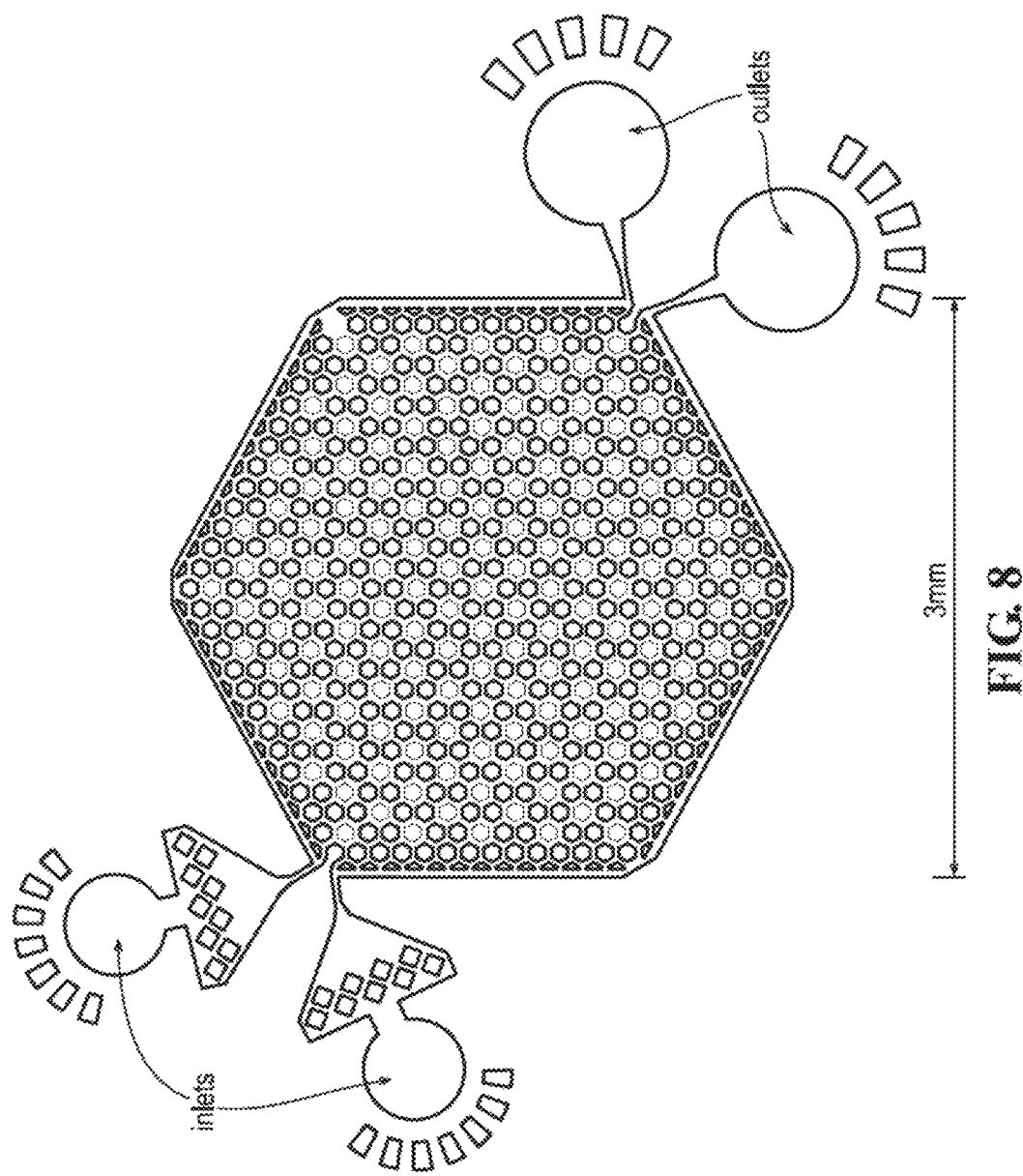
FIG. 8 illustrates another embodiment of a controlled fluidic device design.
Figure 9:
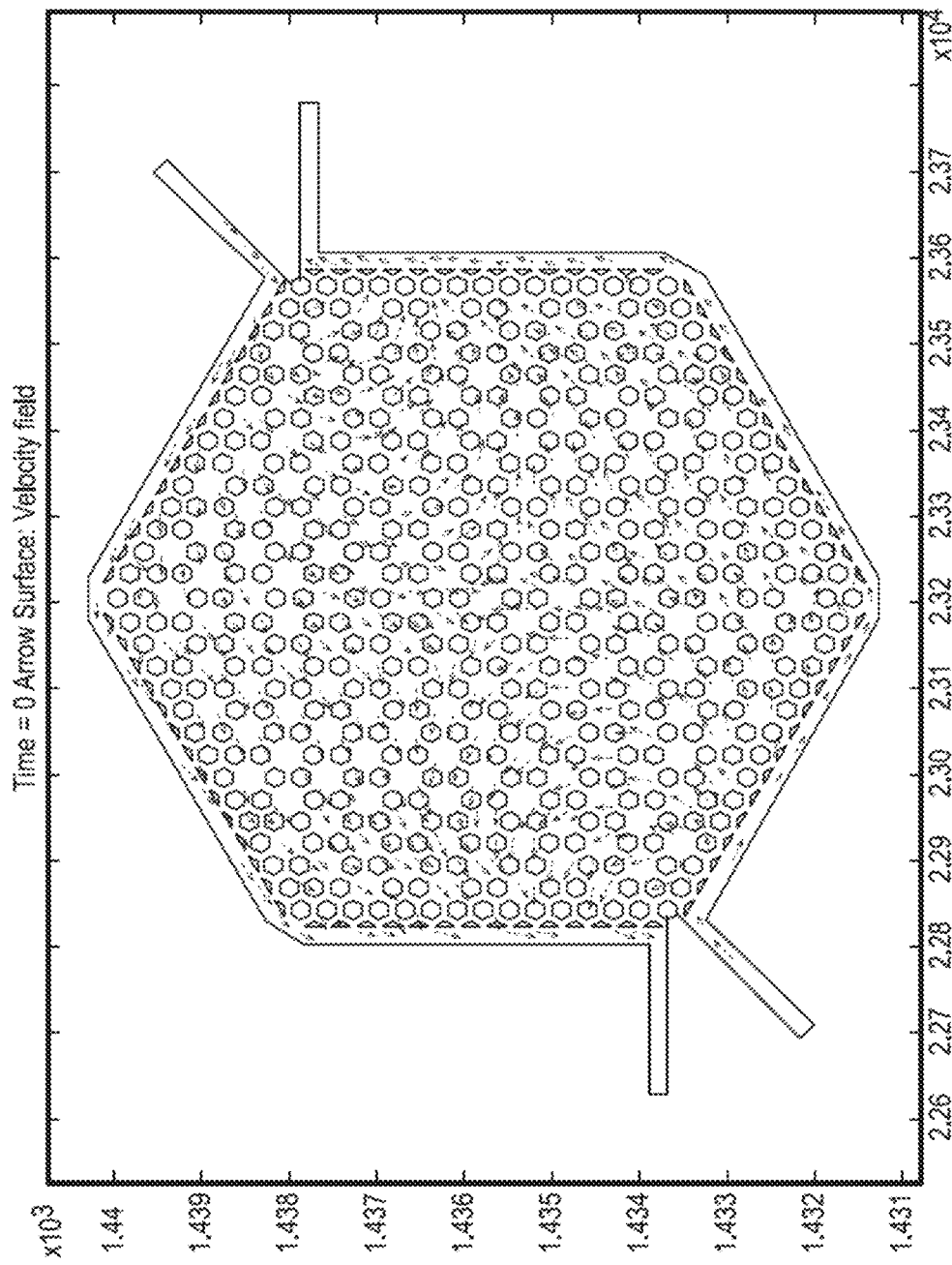
FIG. 9 illustrates a controlled fluidic device design where the inlets are on the opposite sides and the vectors are the flow velocity.
Figure 10:
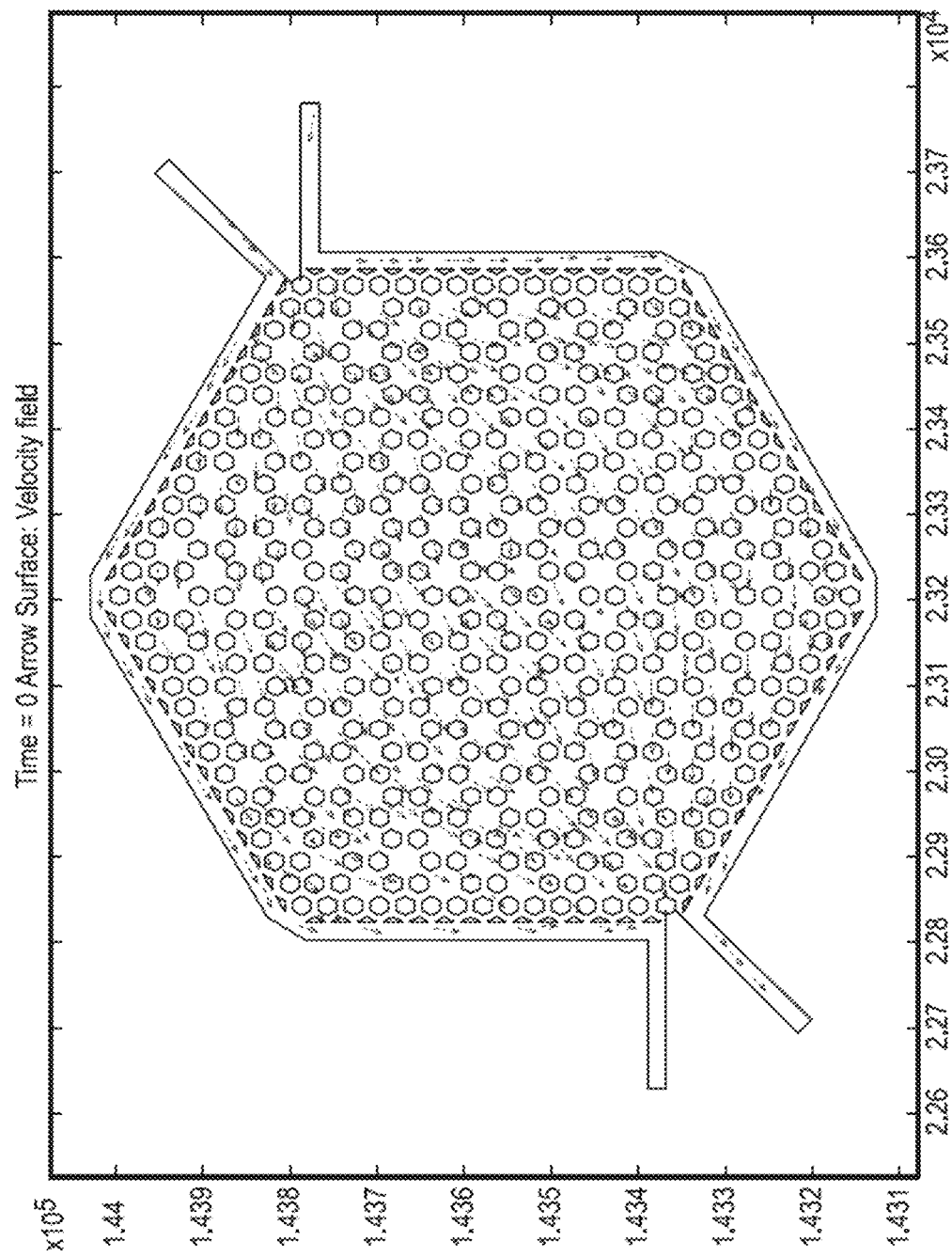
FIG. 10 illustrates a controlled fluidic device design where the inlets are on the same side and the vectors are the flow velocity.
Figure 11A:
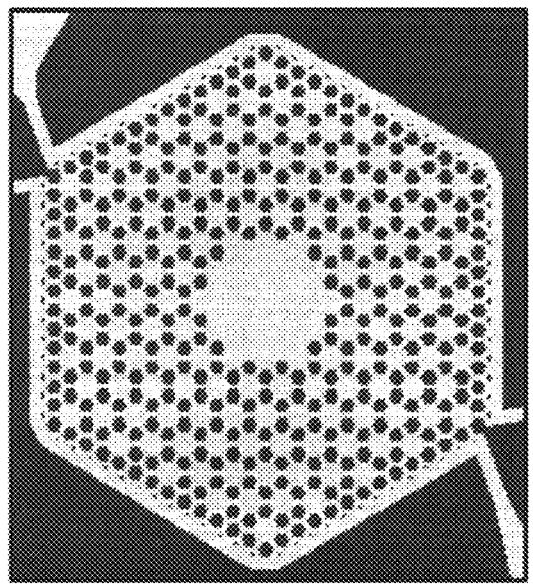
FIG. 11A is a schematic image of a gradient chamber.
Figure 11B:
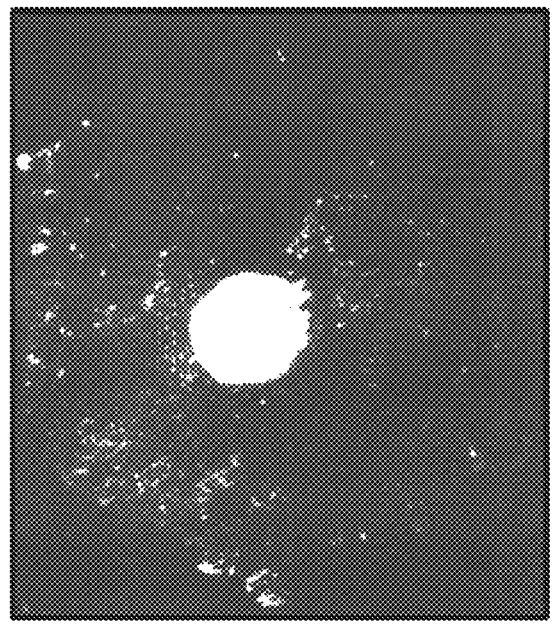
FIG. 11B is a fluorescent microscopy image of the gradient chamber stained to show growth or *E. coli* growing in a gradient of nitric oxide.
Figure 12A:
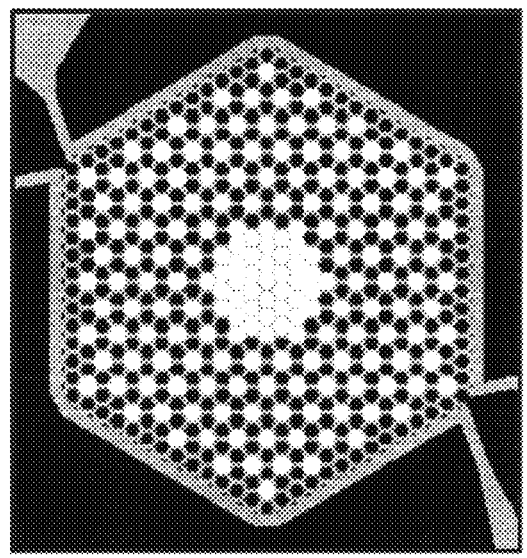
FIG. 12A is a schematic image of a gradient chamber, with the highlighted regions showing the location of recessed wells within the device.
Figure 12B:
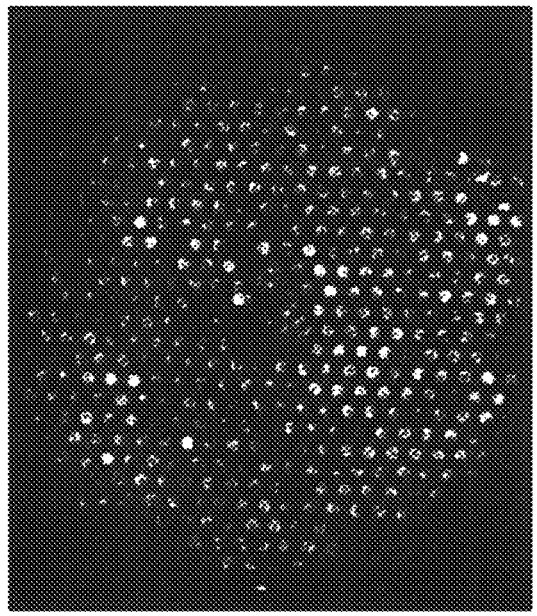
FIG. 12B is a fluorescent microscopy image (bottom) stained to show growth of *C. albicans* under a gradient of growth media in the gradient chamber, in accordance with certain example embodiments.

Turning to FIG. 2, the interior elements of the gradient chamber 105 are discussed in more detail. In certain example embodiments, the chamber 105 may comprise a plurality of recessed regions 125 interspersed between a plurality of raised portions or columns or posts 130. The columns 130 may have a cross section of between 10 to 125 μm. The recessed regions 125 may be in fluid communication such that fluids may flow between the columns 130. The spacing of the columns to arrive at different configurations, for example, to capture certain substrates or cells. In certain example embodiments, the depressed regions 125 may form a well, therefore the term recessed region and well are used interchangeably herein. In certain example embodiments, the well 125 have a depth of 5 to 500 μm. For wells 135 intended for the culturing prokaryotic cells the depth may be 25 μm to 30 μm. For wells 135 intended to culture eukaryotic cells, the depth may be 50 μm to 100 μm. In certain example embodiments involving a two-sided chamber, a recessed region 125 on one side may form a column on the opposite 130 on the opposite side. In certain example embodiments, the chamber 105 may comprise a cluster of wells 125 at the center of the chamber, as show in FIG. 2. The number of individual wells 125 that may be defined within a given chamber 105 may be between 1 and 2000 wells per gradient chamber. In certain other example embodiments, the chamber 105 may have a single continuous depressed region or larger well defined at the center of the chamber. In certain other example embodiments, the gradient chamber 105 may have an opening through the center of the gradient chamber 105. See FIGS. 5 and 6.

Figure 3A:
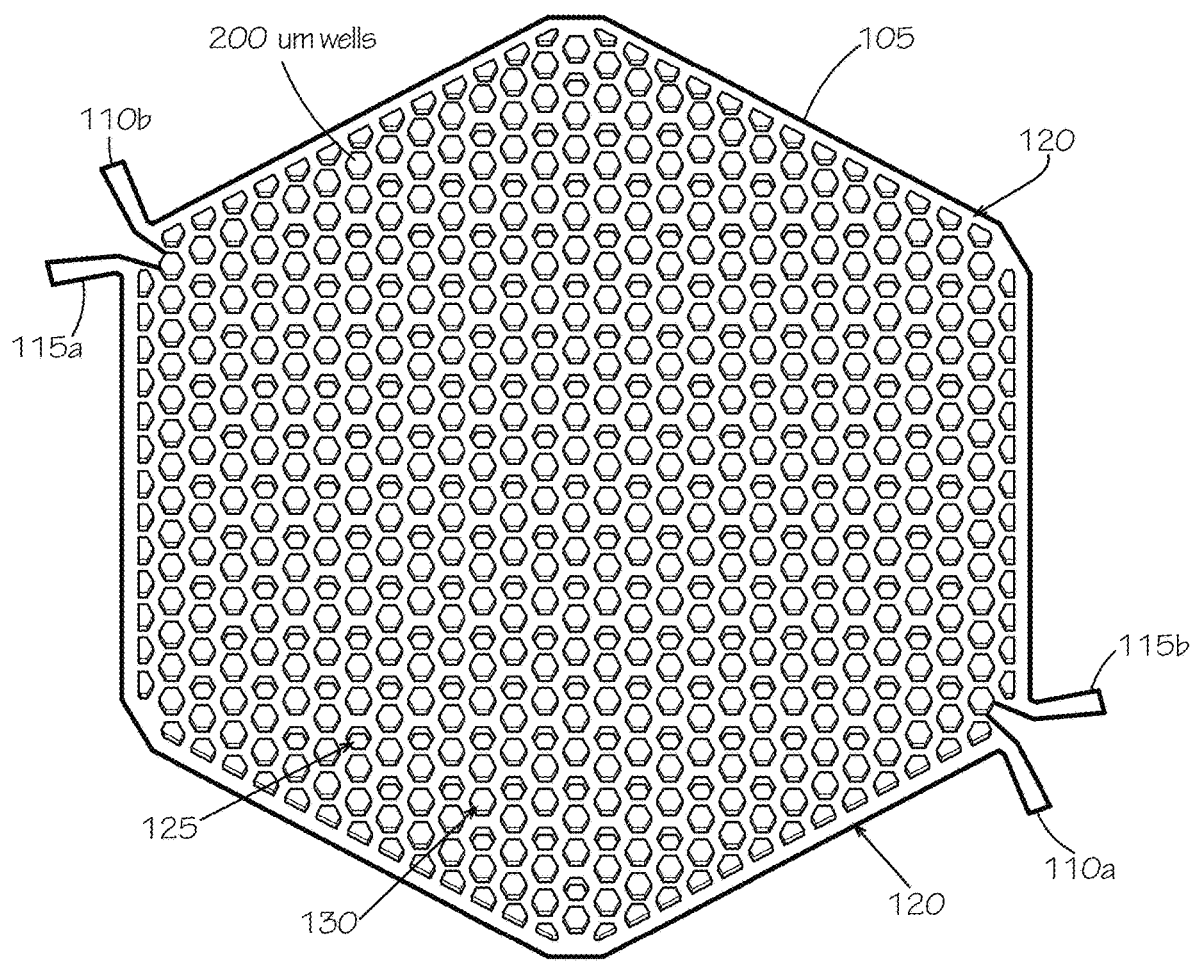
FIG. 3A is a diagram of an alternative interior layout of a chamber in accordance with certain example embodiments.
Figure 3B:
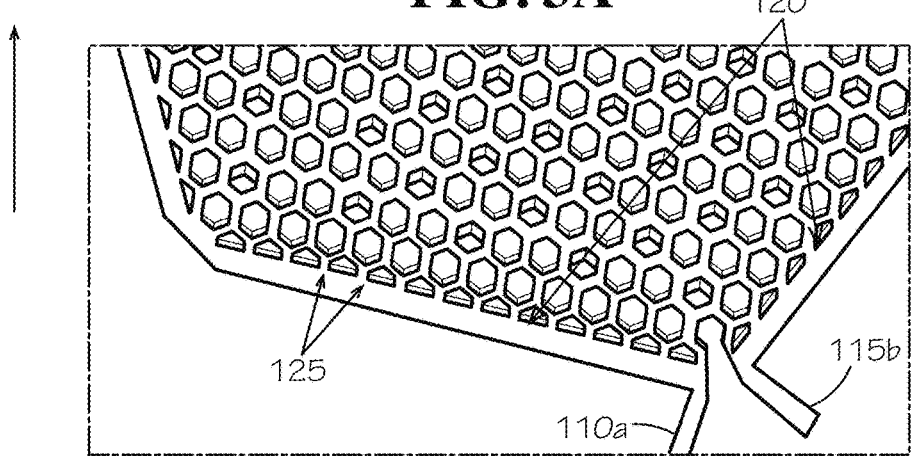
FIG. 3B is an exploded section of FIG. 3A.
Figure 4:
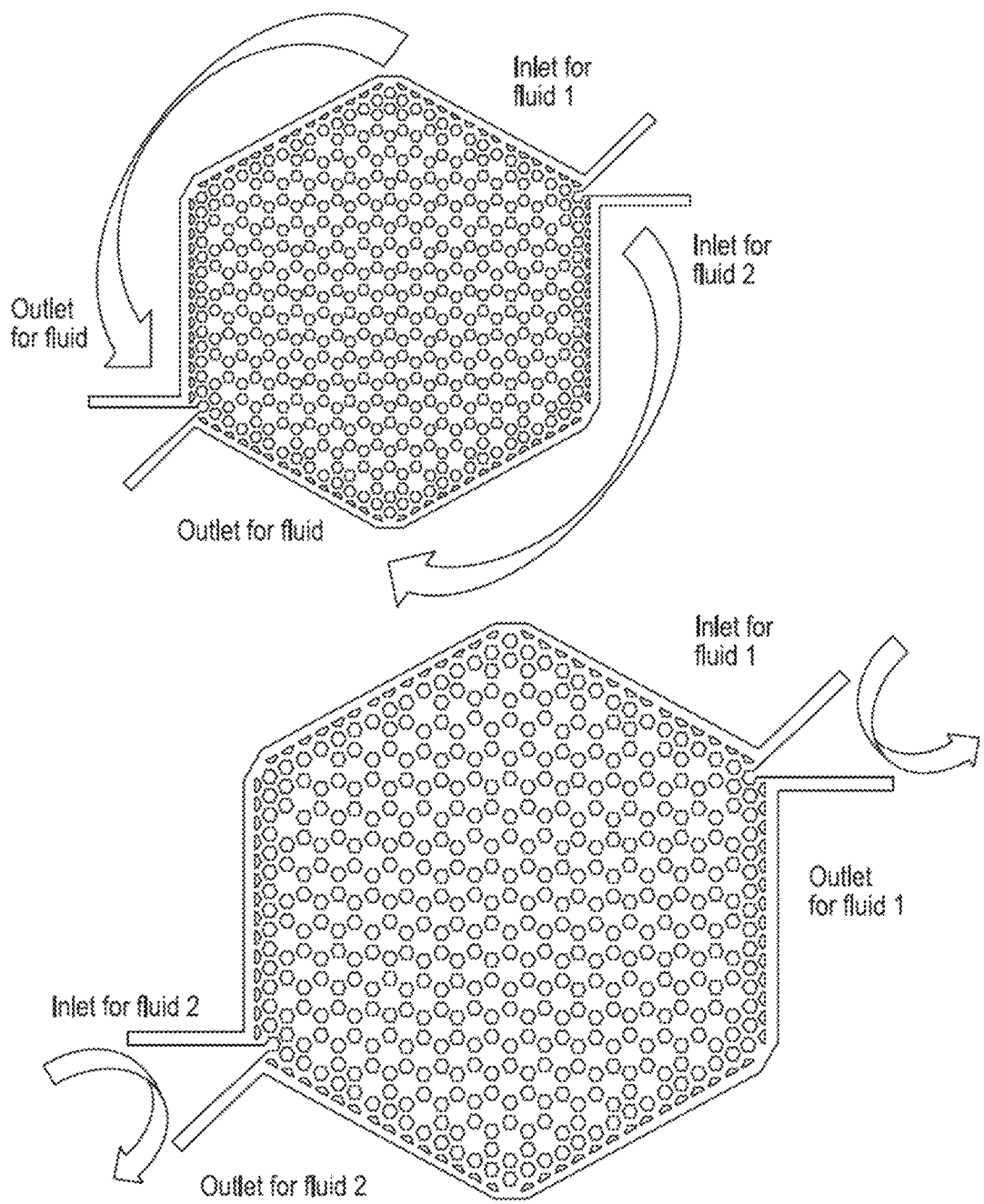
FIG. 4 illustrates flow simulation for a controlled fluidic device design.

FIG. 3A provides an alternative embodiment where the interior of chamber 105 is defined by an alternating pattern of wells 125 and columns 130. FIG. 3B provide an exploded section of FIG. 3A, showing where the peripheral channel 120 connects to an inlet 110a and outlet 115b. In this particular embodiment, inlet 110a is connected to outlet 115a by a first peripheral channel 120, and inlet 110b is connected to outlet 115b via second peripheral channel on a side opposite that of the first peripheral channel.

In certain example embodiments, the interior of each chamber 105 may further comprise a coating. In certain example embodiments, the coating may be applied to only the wells 135. The coating may comprise collagen, agar, and mucin.

Figure 17:
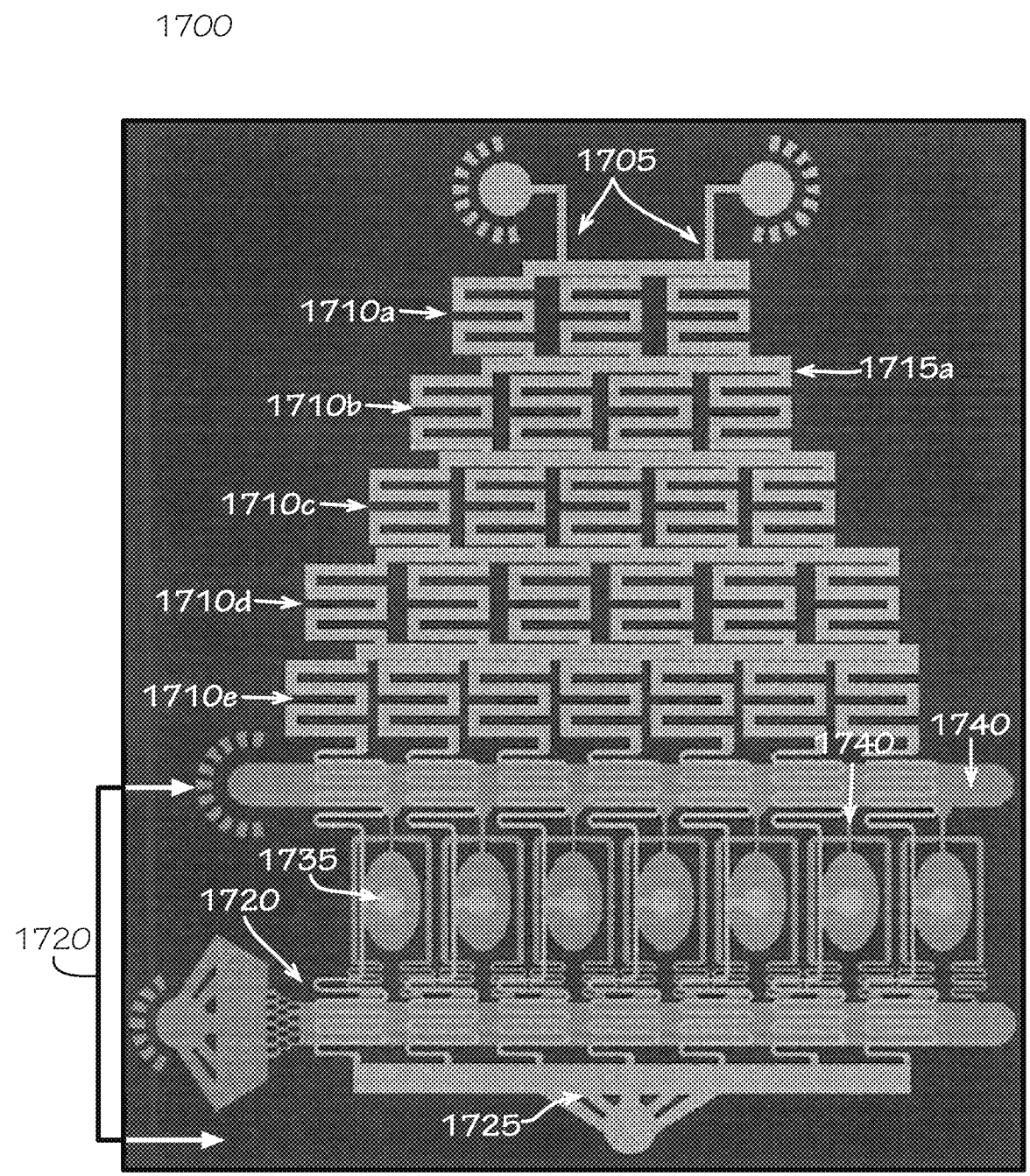
FIG. 17 is a schematic stacked set of resistor lines (droplet tree), in accordance with certain example embodiments.
Figure 18A:
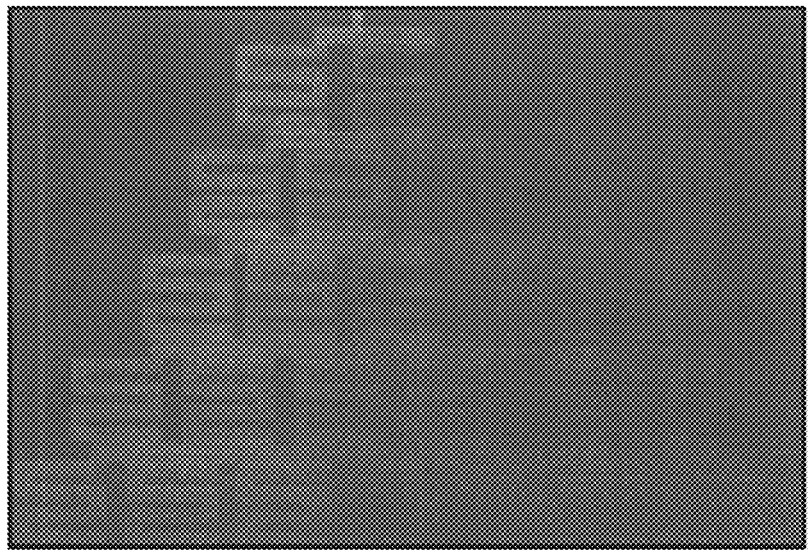
FIG. 18A is a fluorescent image of an example droplet tree configuration loaded with fluorescent dye and demonstrating the differing concentration of dies that form moving left to right as the die solution is flowed through a device and an image of a set of droplet modules, in accordance with certain example embodiments.
Figure 18B:
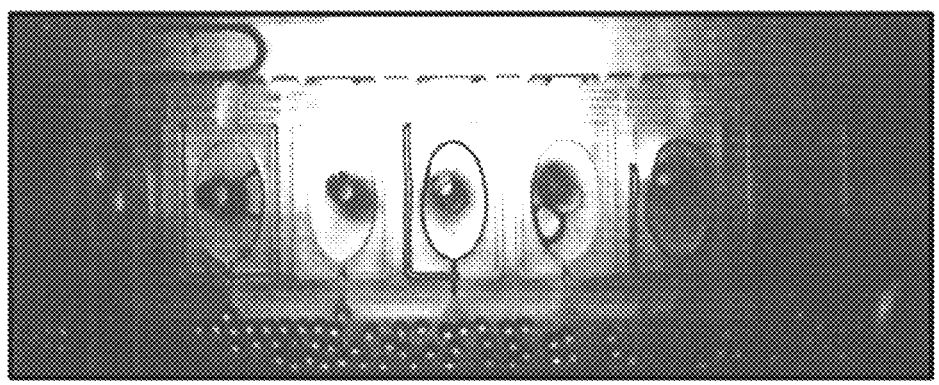
FIG. 18B is an image of the device.
Figure 19A:
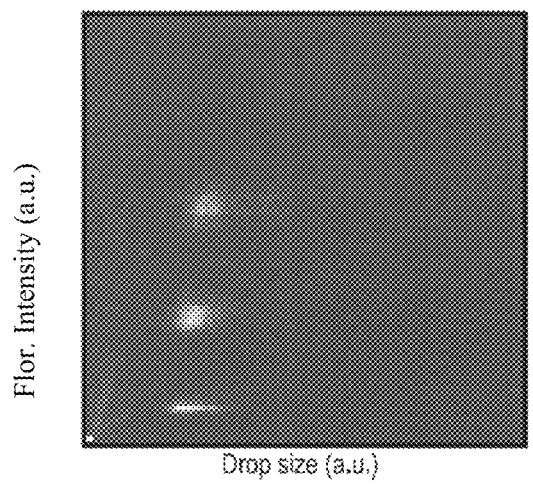
FIG. 19A is a heat map representing the number of drops formed using an example droplet tree device disclosed herein with different concentrations of drug.
Figure 19B:
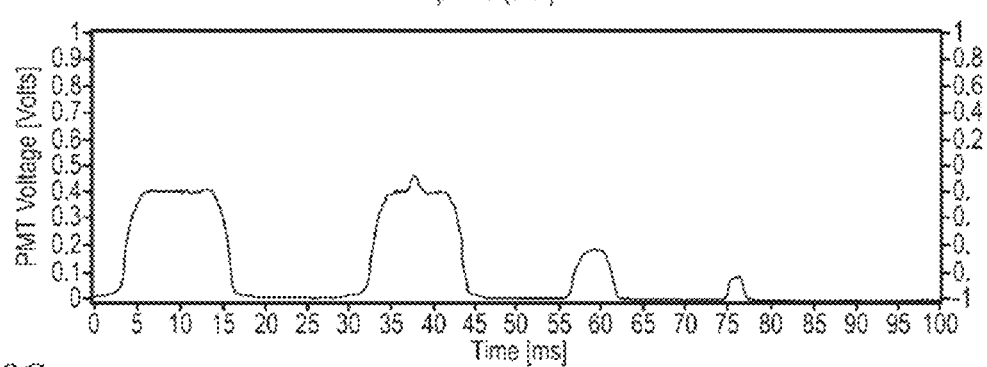
FIG. 19B is a time trace of droplet intensity.
Figure 19C:
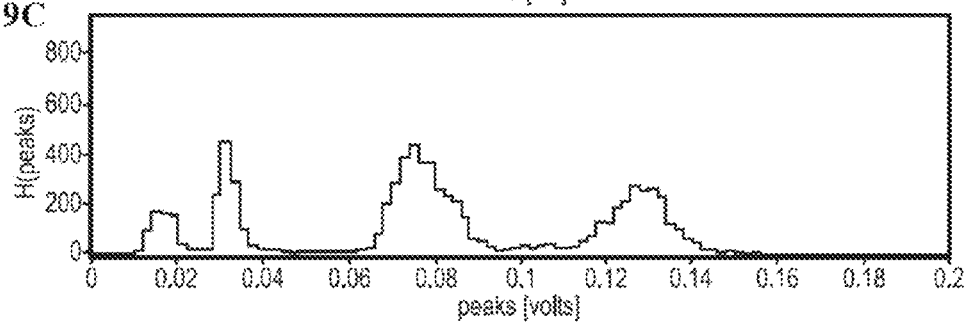
FIG. 19C is a graph of droplet distribution over fluorescence concentration.

Turning to FIG. 17, in certain example embodiments, the device may comprise one or more a set of stacked resistor lines optionally connect to one or more droplet modules ("droplet tree"). The droplet tree 1700 may comprise two or more inlets 1705 for receiving multiple solutions. For example, a first solution may comprise a drug to be screened and the second solution a diluent or carrier for establishing different concentrations of the drug. The solutions may then flow from the inlets into a first row or level of resistor lines 1710a. The resistor lines 1710 may comprise multiple bends or turns. In certain example embodiments, these turns may comprise multiple 180° turns that reverse the direction of the flow of the solution as it passes through the resistor line. FIG. 18A shows the flow of a fluorescent solution through an example droplet tree and the varying concentrations that set up across the resistor channels as the solutions mixes across the various levels of the droplet tree. The first row of resistor lines 1710a may be connected to a second row of resistor lines 1710b via a channel 1715a and so one between each level. In general, the number of resistor lines increases with each successive row and may be connected by additional channels 1715. The shape and design of the resistor lines may be the same across all rows, or may vary between rows.

In certain example embodiments, the width and height of the resistor lines and connecting channels may be between 0.5 μM and 500 μM. In one example embodiment, the each resistor line comprises three turns per resistor line. In general, each successive row adds one additional resistor line to the number of individual resistor lines 1710 in the proceeding row to which it is connected. In certain example embodiments, the total number of rows per droplet tree component may range from 3 to 20.

In certain example embodiments, the stacked set of resistor lines described above may then connect to one or more gradient chambers described herein. In certain example embodiments, a single resistor line in a final row of the droplet tree may connect to a single gradient chamber. In certain other example embodiments, multiple resistors lines may connect to a single gradient chamber. Thus, a gradient or gradients resulting from multiple input concentrations derived by flow through the stacked resistors may screened simultaneously.

In certain example embodiments, the droplet tree comprises further elements for fusing droplets of different concentrations with cells for droplet based screening, collectively referred to as a droplet formation module 1720. In this way multiple droplet libraries, each library having a different set of concentrations, may be screened in multiplex fashion. For example, replicates of a cell library comprising cells that each have a different genetic perturbation may be screened for the impact of that genetic perturbation across multiple droplets by merging each cell library replicate with a droplet library comprising a different set of culture conditions (e.g. drug concentrations, growth factor concentrations, etc.).

In certain example embodiments, the droplet formation module 1720 comprise, a cell distributor 1725, a carrier oil distributor 1730, one or more droplet formation chamber 1735, and a collection line or reservoir 1740. The cell distributor inlet distributes cells to each droplet formation module 1735, where the cells mix with the final solution flowing from each resistor 1710e in the final row of resistor lines. In certain example embodiments, the droplet formation chamber is double layers. The cells and final solution meet on a top layer of the chamber and then drops to a second layer of the chamber 1735. The carrier oil is introduced via the carrier oil distributor 1730 to a droplet formation interface 1745 connected to a bottom layer of the droplet formation chamber 1735. Droplets form at the droplet interface 1745 and then flow into the collection line or reservoir 1740. In certain example embodiments the carrier oil distributor 1730 and collection line 1740 are on the same layer as the lower layer of the droplet formation module 1720. As shown in FIG. 17 additional resistor lines may be used to connect the cell distributor 1725, carrier oil distributor 1730, droplet formation chamber 1735, and collection reservoir 1740 to one another. The resistor lines may have a width of between 50-100 μM. In certain example embodiments, the width of the resistor lines 1710 is at least 100 μM.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/ mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In an another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons. Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets within the droplet library provided by the instant invention may be uniform in size. That is, the diameter of any droplet within the library will vary less than 5%, 4%, 3%, 2%, 1% or 0.5% when compared to the diameter of other droplets within the same library. The uniform size of the droplets in the library is critical to maintain the stability and integrity of the droplets and is also essential for the subsequent use of the droplets within the library for the various biological and chemical assays described herein.

The droplets comprised within the emulsion libraries of the present invention may be contained within an immiscible fluorocarbon oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The droplet libraries of the present invention are very stable and are capable of long-term storage. The droplet libraries are determined to be stable if the droplets comprised within the libraries maintain their structural integrity, that is the droplets do not rupture and elements do not diffuse from the droplets. The droplets libraries are also determined to be stable if the droplets comprised within the libraries do not coalesce spontaneously (without additional energy input, such as electrical fields described in detail herein). Stability may be measured at any temperature. For example, the droplets are very stable and are capable of long-term storage at any temperature; for example, e.g., −70° C., 0° C., 4° C., 37° C., room temperature, 75° C. and 95° C. Specifically, the droplet libraries of the present invention are stable for at least 30 days. More preferably, the droplets are stable for at least 60 days. Most preferably, the droplets are stable for at least 90 days.

The present invention provides an emulsion library which may comprise a plurality of aqueous droplets within an immiscible fluorocarbon oil which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil which may comprise at least one fluorosurfactant thereby forming an emulsion library.

Figure 20:
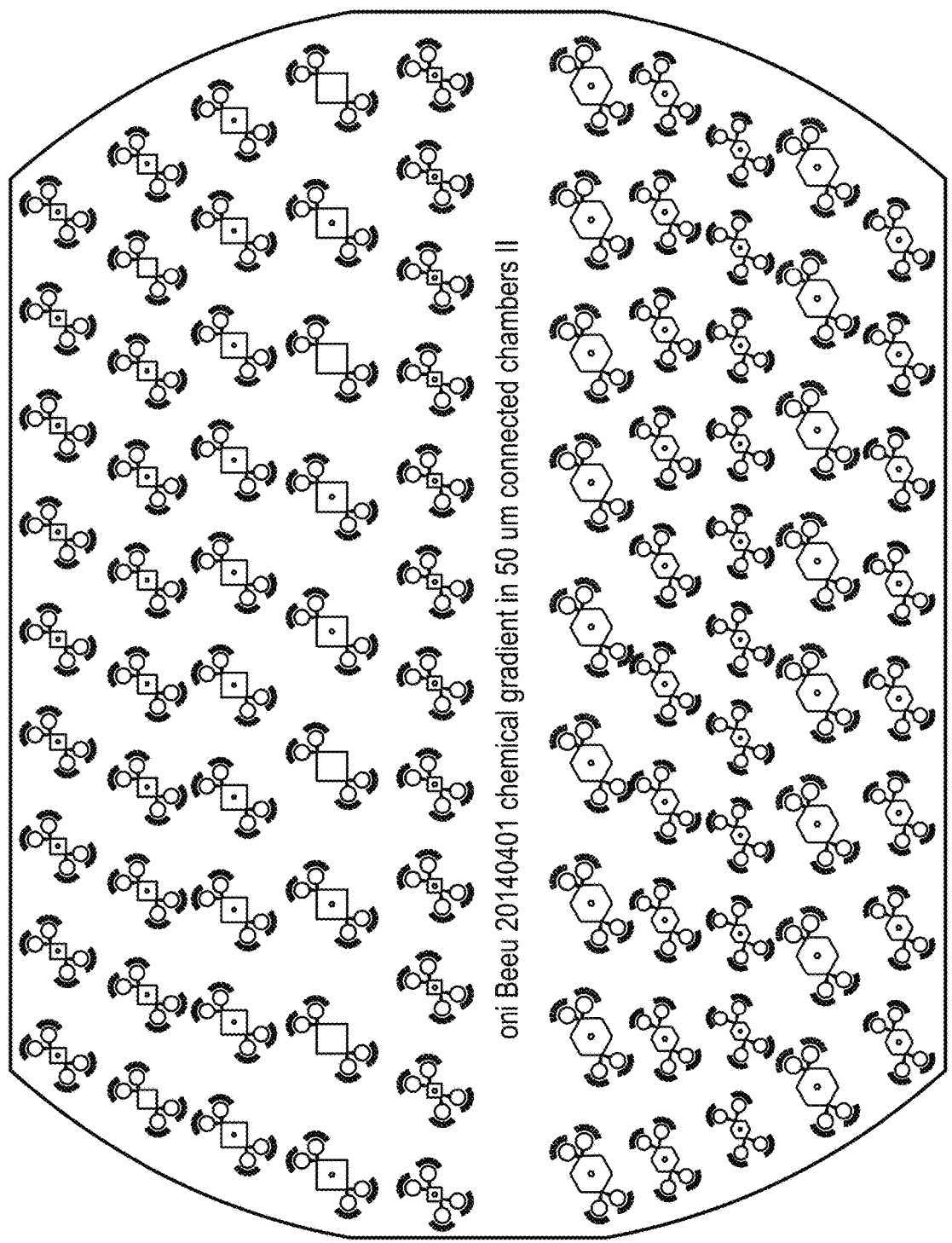
FIG. 20 is a schematic showing an example layout of multiple concentration gradient components arrayed on a single device, in accordance with certain example embodiments.
Figure 21:
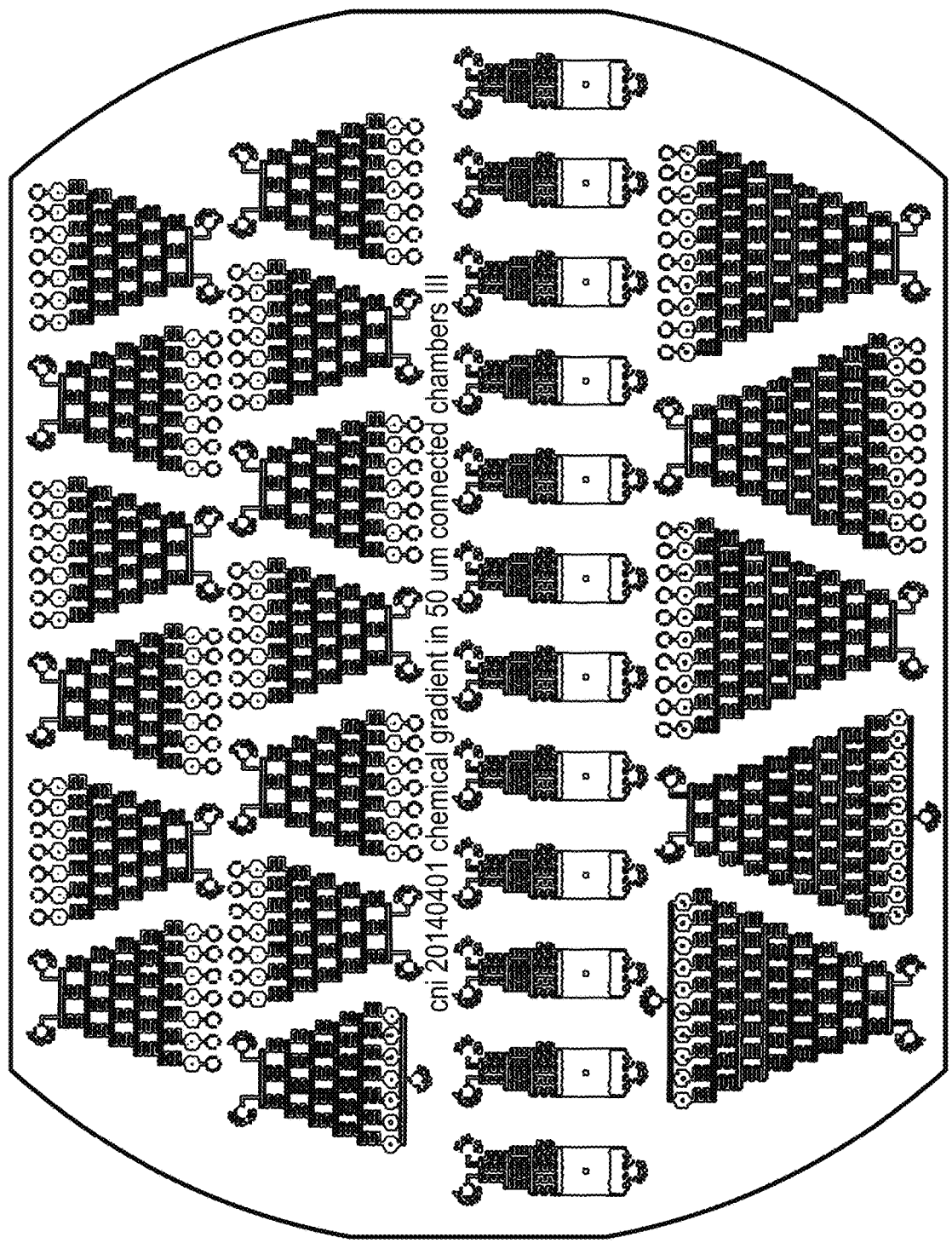
FIG. 21 is a schematic showing an example layout of multiple droplet tree and concentration gradient components arrayed on a single device, in accordance with certain example embodiments.
Figure 22:
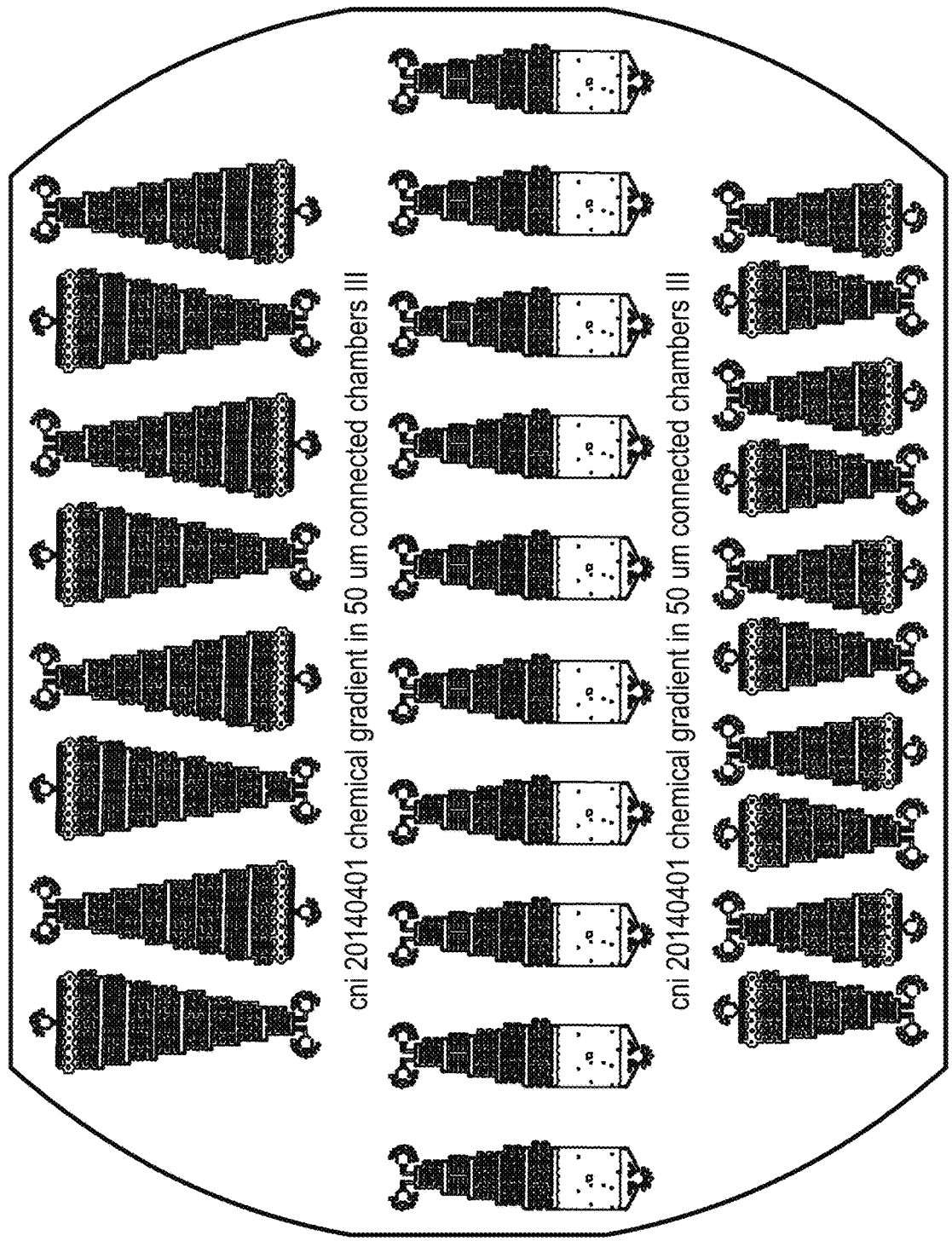
FIG. 22 is a schematic showing an example layout of multiple droplet tree and concentration gradient components arrayed on a single device, in accordance with certain example embodiments.
Figure 23:
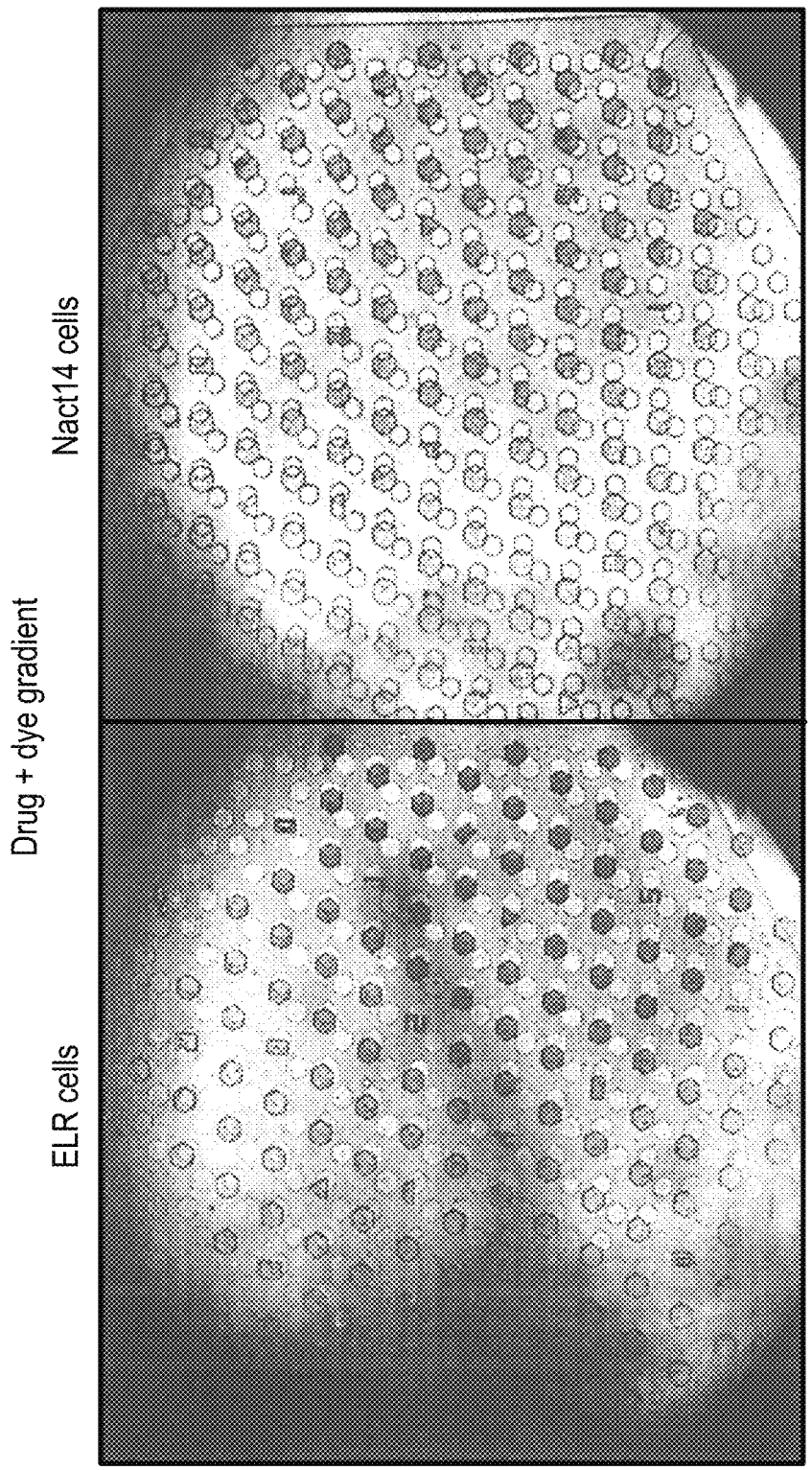
FIG. 23 is an image of a ELR cells (left) and Nact14 cells (right) growing in an example concentration gradient device. A drug concentration was introduced to the device and cells were subsequently stained using Trypan blue. The image demonstrates formation of a drug concentration gradient on the device as evidence by the localized and varying intensity of Trypan blue uptake in dead cells in only a subset of the wells within the gradient chamber.

In certain example embodiments, the resistor lines connect to a gradient chamber instead of a droplet module. Multiple droplet tree and gradient chamber components may be arrayed on a single device substrate. Example configurations are shown in FIGS. 20-21. Each gradient chamber or droplet tree component may have an identical configuration, or a device may comprise components of different sizes and configurations.

Device Applications

The embodiments disclosed herein enable screening of biological systems in a spatially complex environment and/or multiplex screening across a range of different concentrations. The gradient chambers described herein enable the establishment of a gradient within the chamber by controlling the flow of two or more solutions into the gradient chamber at different flow rates.

In certain example, the embodiments disclosed a method of screening one or more cells types for one or more biological functions comprises culturing one or more cell types in a gradient chambers disclosed herein. A gradient is then established within the gradient chamber by controlling the flow rate of one or more solutions into the gradient chamber. The gradient may be a temperature gradient, a concentration gradient, or a combination thereof. In certain example embodiments, a concentration gradient may be formed by flowing in a test solution to be screened and a diluent. Increasing the flow rate of the test solution will set up a broader concentration gradient of the test solution, whereas increasing the flow rate of the diluent will set up a narrower concentration gradient of the agent. See FIGS. 5A-5C. A temperature gradient may be set up in a similar way, by controlling the flow rate of two or more solutions that are at different temperatures Cellular response to the gradient may then be measured.

The measured cellular response to the gradient may included detecting changes in expression of certain RNA molecules, production of certain proteins, lipids, polysaccharides, metabolites, small molecules, or other biological molecules. The measured cellular response may include the effect of the gradient to induce or inhibit expression in the one or more cell types, to induce phenotypic changes in the cell (changes in cell membrane or cell wall morphologies, axonal growth, change in nuclear or organelle morphologies, changes in cytoskeletal arrangement and/or vesicle trafficking), changes in cell motility, including chemotaxis in response to the gradient, the ability to induce or inhibit cell growth, the ability to induce cell death, and/or the ability to induce neoplastic transformation.

In certain example embodiments, the devices disclosed herein are designed for use with light and fluorescent microscopy so that the above cellular responses may be monitored using light and/or fluorescence microscopy techniques known in the art, including live cell microscopy.

The above cellular responses may also be monitored by the inclusion of one or more reporter systems. The reporter system may be a reagent or set of reagents that generate a detectable readout upon interaction with a target protein, nucleic acid, metabolite, lipid, polysaccharide, a small molecule, or other indicator of cellular response or desired biological function produced by a microscale biological system. In certain example embodiments, the reporter system produces a detectable signal upon detection of a particular biological function. The detectable signal may be a colorimetric signal, such as a change in color by a pH indicator. In certain example embodiments, the reporter element may comprise one or more detectable labels. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, ß-galactosidase, urease, alkaline phosphatase or peroxidase, avidin/biotin complex. In certain example embodiments, the detectable label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4', 6-diamidino-2-phenylindole (DAPI); 5'5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2', 7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl.

Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to. Thus, as a non-limiting example, RNA transcripts from the cell may be ligated to one or more tags, which may be sequenced and correlated with conditions that the corresponding droplet or cell to determine information such as apoptosis gene signatures, growth arrest signatures, immune signatures, metabolic gene sets, or expression of genes that confer susceptibility or resistance to other known agents, etc.

Cells to be screened by the methods disclosed herein may be eukaryotic cells, prokaryotic cells, or plant cells. In certain example embodiments, the cells may be naturally occurring. In certain example embodiments, the cells may be isolated from clinical isolates. Any suitably clinical isolate may used in the present invention including, but are not limited to, a biopsy or other tissue sample, a blood sample, a saliva sample, and a urine sample. In certain example environments the cells may be isolated from an environmental sample. Environmental samples include, but are not limited to household/commercial/industrial surfaces (metal, wood, plastic), soil samples, and water samples (fresh and saline). In certain example embodiments, the cells may be engineered to comprise one or more genetic perturbations. For example, the sample set could comprise a set of cells, each cell carrying a different genetic perturbation or combination of genetic perturbations to be screened. Genetic perturbations may include gene knock-outs, gene knock-ins, transpositions, inversions, and/or one or more nucleotide insertions, deletions, or substitutions.

In certain example embodiments, the gradient chamber is made from materials that can allow a cell population growing in a given well to be punched out of the device for further analysis. For example, one or more wells comprising cells exhibited a desired biological activity or cellular may be punched out like a biopsy punch out and further analysis, such as sequencing or nucleic acid amplification analysis, may be conducted on the cells. In certain other example embodiments, a lysis solution may be flowed into the gradient chamber to lyse all cells in the gradient chamber and then flushed to extract the lysate from the gradient chamber for further analysis or isolation of biomolecules from the cells.

In one example embodiment a method for evaluating response in a cell population comprises: introducing a cell population into the gradient chamber; administering the two or more different fluids into the closed chamber via the two more inlet ports such that a concentration gradient is established in the closed chamber; and, measuring the response of the cell population at various concentrations across the concentration gradient. In certain example embodiments, a test solution may be mixed with a diluent solution within the gradient chamber to create a gradient of the test solution. The test solution may comprise one or more agents. The one or more agents may be cell growth media agents, cell signalling biomolecules, therapeutic agents, or other agents to which a cellular response is measured. Diluent solutions may be aqueous solution and may be any diluent solution in the art suitable for use with the assay to be carried out within the gradient chamber.

In one example embodiment, a method of screening cellular response to one or more therapeutic agents comprises: introducing a cell population into the gradient chamber; administering a test solution comprising the therapeutic agent and a diluent solution to establish a gradient of the one or more therapeutic agents within the concentration gradient; and measuring the response of the cells to the various concentrations of the one or more therapeutic agents.

Figure 13:
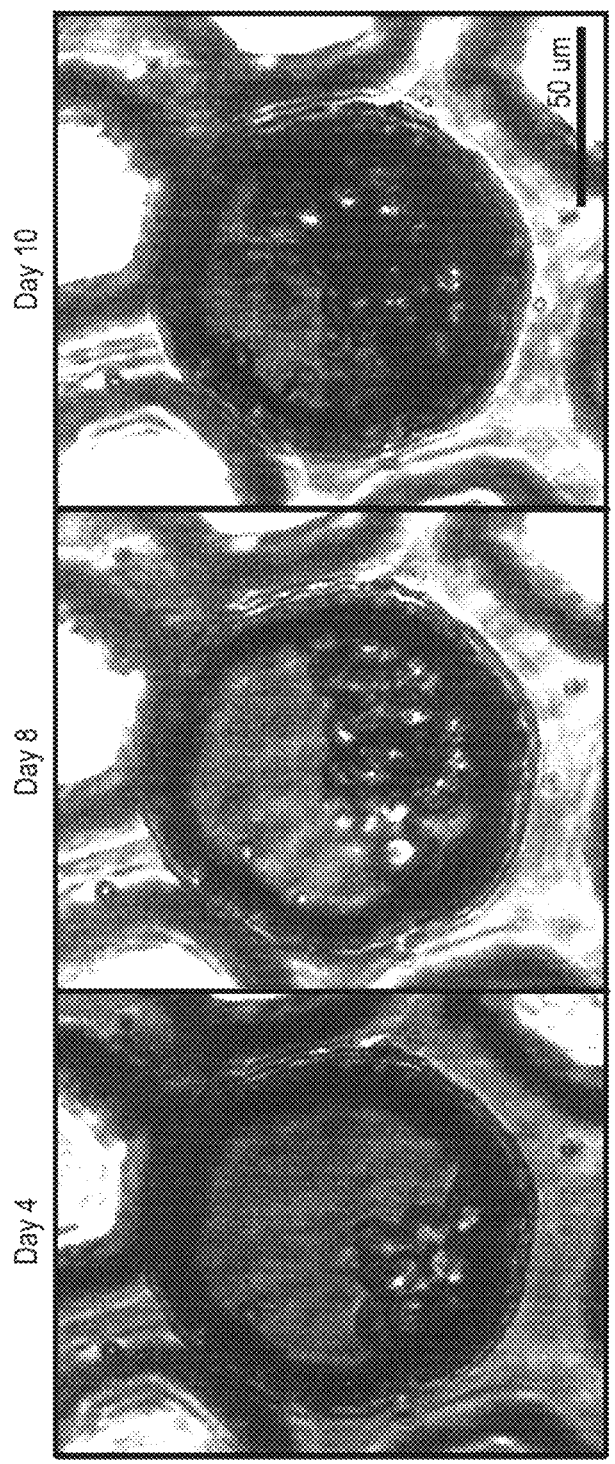
FIG. 13 is an image showing transformed cells growing in no-attachment in wells located in a chamber of an example device.
Figure 14:
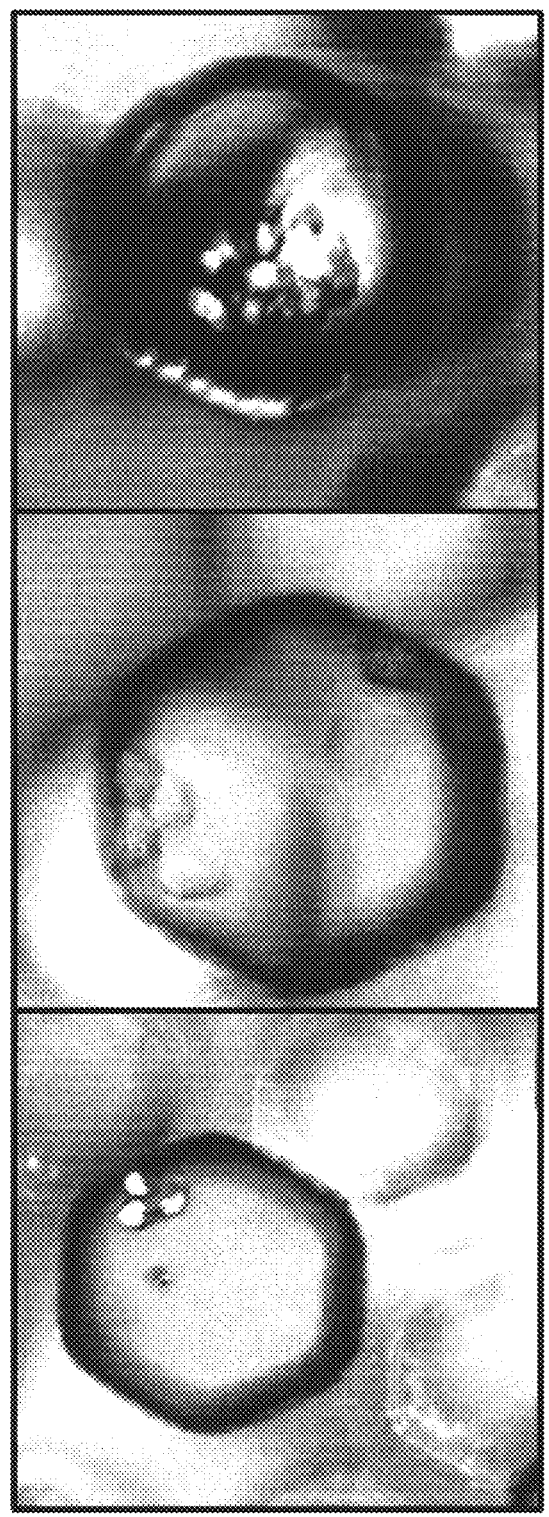
FIG. 14 provides a set of images of transformed fibroblasts cultured in wells of an example device. Hoechst-stained nuclei allow for detection (and counting) of single cells, even hidden cells that would be missed otherwise. Apoptotic cells with small fragmented nucleic were also observed. Calcein was used to stain viable cells.
Figure 15:
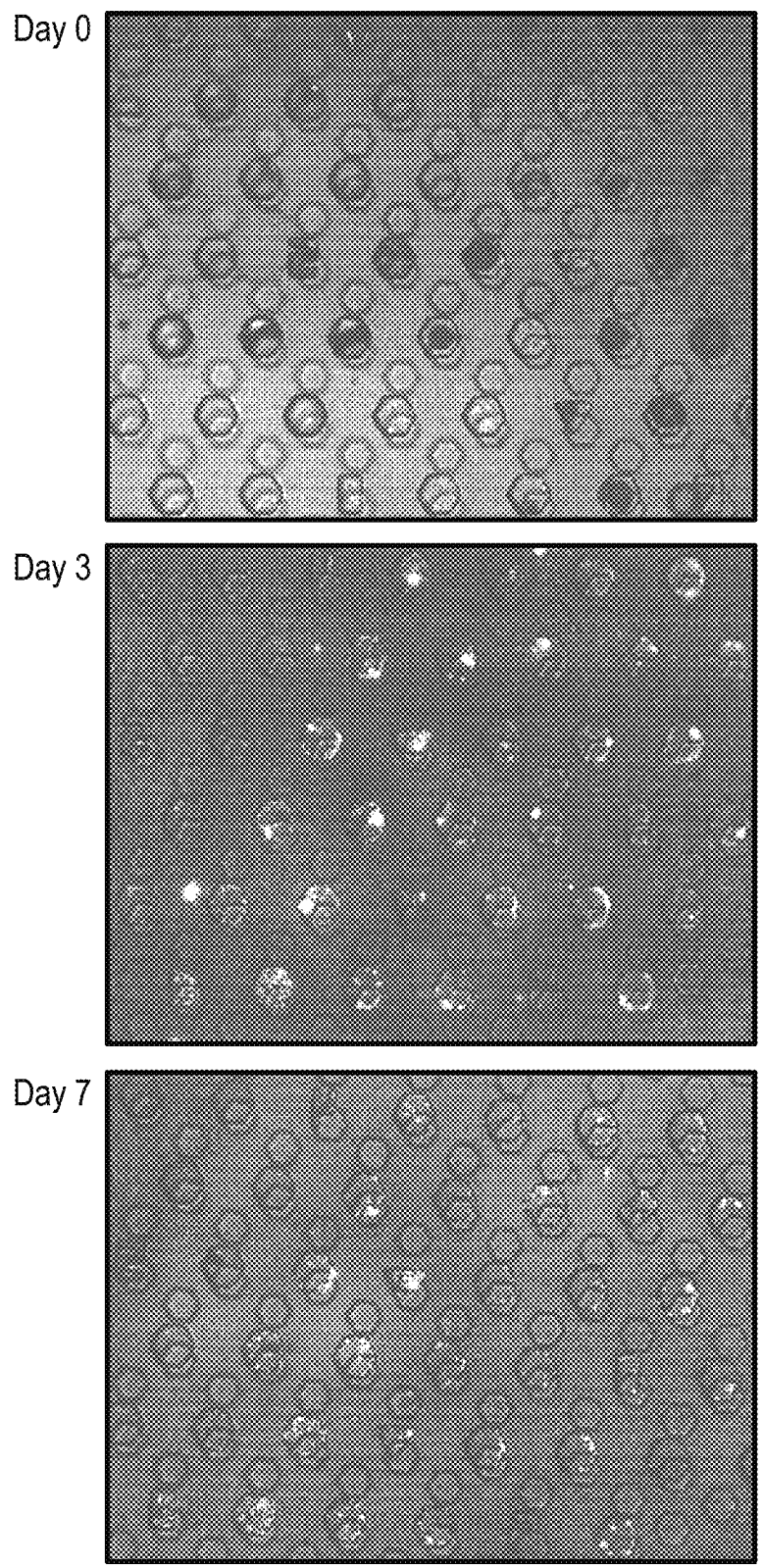
FIG. 15 provides a set of images showing primary cells (Nact8) collected from fluid accumulation in ovarian cancer patients then expanded in wells of an example gradient chamber. The cells are shown at day 0 (top), day 3 (middle) and day 7 (bottom). The cells are stained with Hoechst. The hexagonal wells are 200 μm wide and 100 μm deep.
Figure 16:
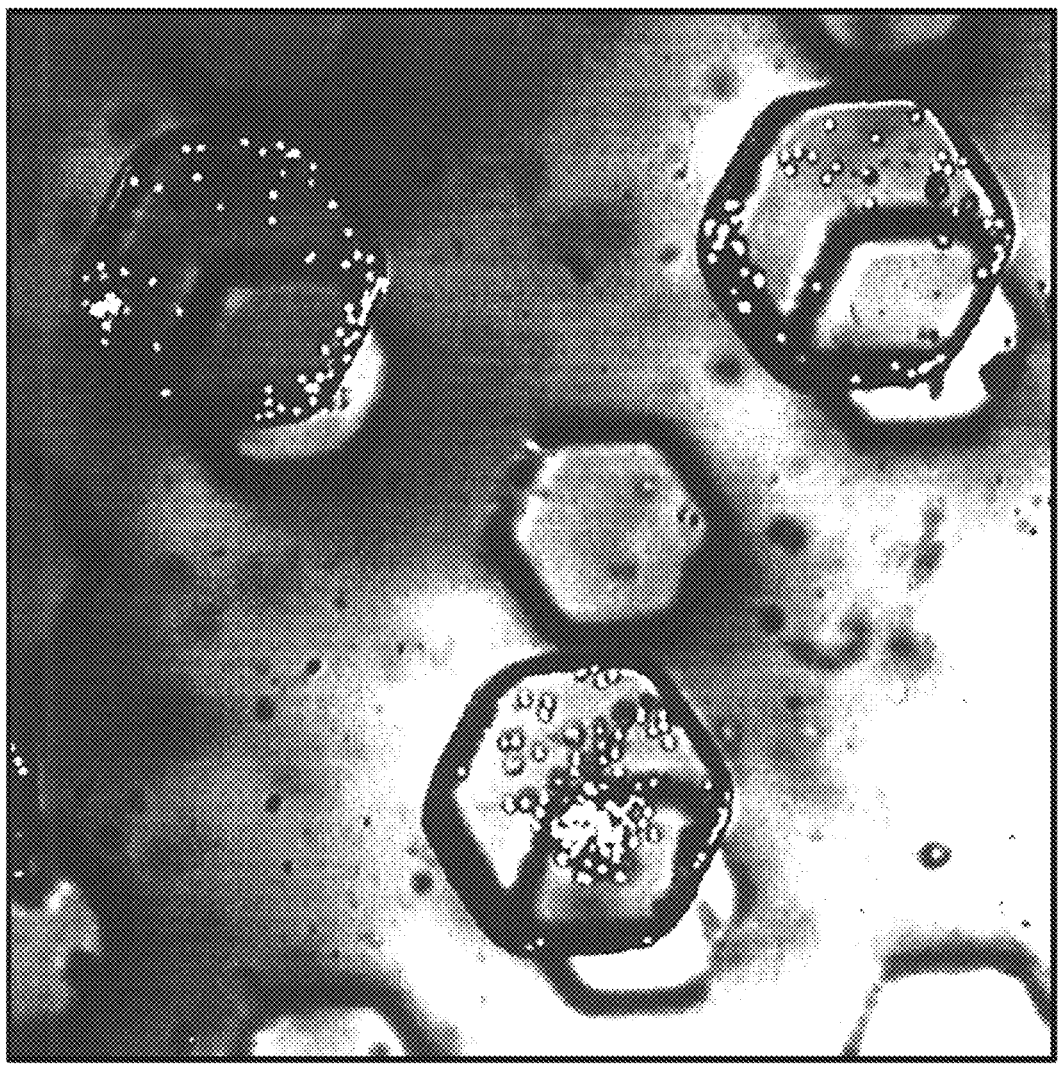
FIG. 16 provides a confocal microscope image of the day 3 cells shown in FIG. 14 at higher magnification.

In certain other example embodiments, the devices disclosed herein may be used to conduct growth in low-attachment (GILA) or growth in no-attachment (GINA) assays. These assays may be used to assess drug-sensitivity for limited-size core biopsies. While surgical excisions may have a few hundred million cells in it, and ex vivo drug-sensitivity assays could be done early, the situation for biopsies is the complete opposite. Core biopsy, which is a minimally invasive method to analyse diseased tissue, has an average of 200,000 thousands cells. This core will ultimately yield a very limited number of viable cells. NACT8 cells are ovarian cancer cells, collected from abdominal ascites as part of a neoadjuvant study. FIGS. 15 and 16 shows the successful culturing of said cells in an example gradient chamber as disclosed herein in a no-attachment environment. FIGS. 13 and 14 likewise show culturing of a cell line of transformed fibroblast in an example gradient chamber as disclosed herein. Referring to FIG. 14, Hoechst-stained nuclei (left) allow detection and counting of single cells. Calcein may be used to stain viable cells (middle). A combination of calcein and Hoechst show individual viable cells (right). A dye, such as Trypan Blue, may be used to stain for dead cells.

Thus, in one example embodiment, a GINA drug-sensitivity assay comprises; introducing cells into a low-attachment gradient chamber comprising untreated wells; administering a test solution comprising the therapeutic agent and a diluent solution to establish a gradient of the one or more therapeutic agents within the concentration gradient; and measuring the response of the cells to the various concentrations of the one or more therapeutic agents. In certain example embodiments, the flow characteristics through the gradient chamber prevent cells from attaching to the interior surface, including the wells, of the gradient chamber.

In one example embodiment, a method of identifying altered chemical resistance in a bacterial population comprises: synthesizing a mutant bacterial strain to express fluorescent proteins; introducing a known concentration of the bacterial strain into the gradient chamber; administering the two or more different fluids into the closed chamber via the two more inlet ports; isolating DNA from a single cell; purifying DNA from bacteria; sequencing DNA from bacteria; preparing and sequencing a single composite sequence library; wherein identification of alteration in level of expression compared to a baseline gene expression measurement of at least one biomarker is indicative of chemical resistance, and wherein the baseline gene expression measurement is the gene expression measured in the microfluidic well prior to administration of the two or more different fluids.

As discussed above, the droplet tree components may be used to generate droplets comprising different concentrations of a solution. Thus, the embodiments disclosed herein are also well adapted for use with other existing droplet-based assays, such as single-cell assays, where screening of cellular responses across different growth conditions is desired. For example, droplets comprising a cell or population of cells to be screen may be merged with droplets comprising varying concentrations of a test solution and generated using the droplet tree embodiments disclosed herein, thereby allowing the same assay to be carried out across multiple concentrations simultaneously. Droplet libraries as described above may then be merged with a cell library. A cell library element may include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discreet nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element. Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Cellular responses may then be measured using known droplet based techniques in the art. For example, assays such as Drop-Seq, described in Klein et al. Cell (2015), 161: 1187-1201 and Macosko et al. Cell (2015), 161:1202-1214, may be used to analyse a cellular response through sequencing. Thus, the methods disclosed above regarding use with the gradient chamber may be adapter for use in a droplet context my merging droplets comprising a cell to be screen with droplets generated by the droplet tree module and then assayed for a particular cellular response.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

A cell library element may include, but is not limited to, hybridomas, B-cells, primary cells, cultured cell lines, cancer cells, stem cells, or any other cell type. Cellular library elements are prepared by encapsulating a number of cells from one to tens of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discreet nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

One of skill in the art will recognize that methods and systems of the invention are not limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA.

Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures). Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4-(OCH2-CH2)xOH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, s-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil).

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surround by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid.

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device described herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

A plurality of biological assays as well as biological synthesis are contemplated for the present invention.

In an advantageous embodiment, polymerase chain reactions (PCR) are contemplated (see, e.g., US Patent Publication No. 20120219947). Methods of the invention may be used for merging sample fluids for conducting any type of chemical reaction or any type of biological assay. In certain embodiments, methods of the invention are used for merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In certain embodiments, the first sample fluid will include some or all of the reagents necessary for the PCR whereas the second sample fluid will contain the balance of the reagents necessary for the PCR together with the detection probes.

Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule (Td=2(A+T)+4(G+C)). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid.

Once mixed droplets have been produced, the droplets are thermal cycled, resulting in amplification of the target nucleic acid in each droplet. In certain embodiments, the droplets are flowed through a channel in a serpentine path between heating and cooling lines to amplify the nucleic acid in the droplet. The width and depth of the channel may be adjusted to set the residence time at each temperature, which may be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double stranded nucleic acid in the droplets is fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

After amplification, droplets may be flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In another embodiment, examples of assays are ELISA assays (see, e.g., US Patent Publication No. 20100022414). The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay.

In another embodiment, single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention.

In other embodiments, chemical prototyping and synthetic chemical reactions are also contemplated within the methods of the invention.

Although the present invention and its advantages have been described in detail, it should be understood that various changes, substitutions and alterations can be made herein without departing from the spirit and scope of the invention as defined in the appended claims.

Microfluidic device is fabricated using polydimethylsiloxane (PDMS) from a master made of SU8 photo-resist1. The PDMS device is then plasma-treated to bond with a glass microscope slide (75 mm×50 mm×1 mm). Since we work with a continuous oil phase, the channels are rendered hydrophobic by flowing in Aquapel (Rider, MA, USA) through the oil inlet and flushing out the excess fluid thorough the remaining inlets/outlets using pressurized air. See McDonald, J. C. et al. Fabrication of microfluidic systems in poly(dimethylsiloxane). Electrophoresis 21, 27 (2000).

The embodiments disclosed herein may be understood by reference to the following numbered paragraphs:

1. A controlled fluidic device for establishing a gradient, comprising:
   a closed chamber comprising one or more inlet port(s) that deliver two or more different fluids via separate inlet channels and at least one outlet port wherein the location of the one or more inlet port(s) and the at least one outlet port are located so that the flow of fluids can be controlled within the closed chamber and a gradient of the mixture of the two or more fluids from the two or more inlet ports is established.

2. The controlled fluidic device of paragraph 0, further comprising a plurality of wells, the wells in fluid communication with the inlet ports such that concentration of the mixture of the two or more fluids of each respective well is related to the location of the respective well with respect to the inlet ports.

3. The controlled fluidic device of paragraph 1, further comprising a fluid channel extending between a first of said wells and a second of said wells such that the first of said wells is in fluid communication with the second of said wells.

4. The controlled fluidic device of paragraph 0, wherein one of the two or more fluids is a null solution for forming a concentration gradient of another of the two or more fluids.

5. The controlled fluidic device of paragraph 0, wherein one of the two or more fluids may contain include a substance for which a concentration gradient is formed.

6. The controlled fluidic device of paragraph 5, wherein the substance is capable of being dissolved in one of the two or more fluids.

7. The controlled fluidic device of paragraph 5, wherein the substance is capable of being homogenously carried in one of the two or more fluids.

8. The controlled fluidic device of any of the preceding paragraphs, wherein the closed chamber, the inlet ports, the outlet ports, and the inlet channels are sized to accept magnetic beads.

9. The controlled fluid device of any one of paragraphs 5, 6, and 7, wherein the substance is a chemical or a drug.

10. The controlled fluidic device of paragraph 0, wherein the controlled fluidic device is a polygonal plate having an upper surface and a lower surface and a peripheral plate edge having a predetermined depth.

11. The controlled fluidic device of paragraph 0, wherein at least one of the two fluids includes at least one component for which gradient could be established.

12. The controlled fluidic device of paragraph 10, wherein the at one least component is a drug.

13. The controlled fluidic device of paragraph 10, further comprising another component for which concentration could be established.

14. The controlled fluidic device of paragraph 13, wherein the another component is a drug.

15. The controlled fluidic device of paragraph 10, wherein the at one least component includes at least two subcomponents.

16. The controlled fluidic device according to paragraph 0, wherein the closed chamber comprises a chip.

17. The controlled fluidic device according to paragraph 16, wherein the chip comprises a polygonal plate.

18. The controlled fluidic device of the preceding paragraphs, wherein opposite sides of the polygonal plate are separated by approximately 1.45 mm.

19. The controlled fluidic device of paragraph 17, wherein opposite sides of the polygonal plate are separated by approximately 1.65 mm.

20. The controlled fluidic device of paragraph 17, wherein opposite sides of the polygonal plate are separated by approximately 1.4 mm.

21. The controlled fluidic device according to paragraph 17, wherein polygonal plate is a hexagonal plate.

22. The controlled fluidic device according to paragraph 17, wherein the polygonal plate is a rectangular plate.

23. The controlled fluidic device of any of the preceding paragraphs, comprising 1200 wells.

24. The controlled fluidic device of any of the preceding paragraphs, further comprising at least one peripheral channel.

25. The controlled fluidic device of paragraph 17, wherein the at least one peripheral flow channel is defined by laminar flow of at least one of the fluids in the closed chamber.

26. The controlled fluidic device of any of the preceding paragraphs, wherein a first of said inlet ports for a first of said different fluids is adjacent an outlet port for a second of said different fluids.

27. The controlled fluidic device of any of the preceding paragraphs comprises a plurality of wells and wherein each of the wells has a depth of approximately 10 µm from the upper surface and each of the sides of each of the wells is approximately 200 µm.

28. The controlled fluidic device of any of the preceding paragraphs, further comprising a first well and a second well, and a channel extending between the first well and the second well, wherein the channel is approximately 200 µm long and approximately 10 µm wide and has a depth of approximately 10 µm.

29. The controlled fluidic device of any of the preceding paragraphs, further comprising a peripheral flow channel, wherein each of the peripheral flow channel has a depth of approximately 5 µm to 500 µm.

30. The controlled fluidic channel of paragraph 29, wherein the peripheral flow channel depth is approximately 10 µm to 250 µm.

31. The controlled fluidic channel of paragraph 29, wherein the peripheral flow channel depth is approximately 20 µm to 30 µm for fluids containing bacterial cells.

32. The controlled fluidic channel of paragraph 29, wherein the peripheral flow channel depth is approximately 50 µm to 125 µm for fluids containing mammalian cells.

33. The controlled fluidic device of the preceding paragraphs, wherein the peripheral flow channel has a width of approximately 6 µm.

34. The controlled fluidic device of the preceding paragraphs, wherein each of the peripheral flow channel has a length of approximately 10 µm to 100 µm.

35. The controlled fluidic device of any of the preceding paragraphs, further comprising a plurality of posts between a lower wall of the closed chamber and an upper wall of the closed chamber.

36. The closed fluidic device of paragraph 35, wherein the posts have a cross-section of approximately 50 µm.

37. The controlled fluidic device of paragraph 2, wherein the wells have a cross-sectional width of approximately 45 µm.

38. The controlled fluidic device of paragraph 2, wherein the wells have a cross-sectional width of approximately 115 µm.

39. The controlled fluidic device of paragraph 16, wherein at least one of the one or more inlet ports is at a vertex of the polygonal plate.

40. The controlled fluidic device of any of the preceding paragraphs, comprising a polymer selected from the group consisting of polyacrylamide, polyethylene glycol, acrylonitrile, halogen-bearing polymers, polyvinyl acetate, acrylic elastomers, polystyrene, polyimides, polyamides, polyurethanes, and polysilanes.

41. The controlled fluidic device of any of the preceding paragraphs, comprising polydimethylsiloxane.

42. The controlled fluidic device of any of the preceding paragraphs, wherein the gradient is established within laminar flows of the two or more fluids.

43. The controlled fluidic device of any of the preceding paragraphs, wherein a Reynolds number of the inlet channel is low.

44. The controlled fluidic device of paragraph 43, wherein the Reynolds number of the inlet channel is less than about 1.

45. The controlled fluidic device of paragraph 43, wherein the formula varies with the cross-section of the channel.

46. The controlled fluidic device of paragraph 43, wherein the channels have a rectangular/square cross-section.

47. The controlled fluidic device of paragraph 43, wherein the channels have a circular cross-section.

48. The controlled fluidic channel of any of the preceding paragraphs, wherein the inlet channels are separated by an angle.

49. The controlled fluidic channel of any of the preceding paragraphs, wherein one of the inlet ports and one of the outlet ports are located on opposite sides of the closed chamber.

50. The controlled fluidic channel of paragraph 49, wherein the one of the inlet ports and one of the outlet ports are separate by an angle in the range of 130 to 220 degrees.

51. The controlled fluidic channel of claim 49, wherein the one of the inlet ports and one of the outlet ports are separate by an angle in the range of 150 to 210 degrees.

52. The controlled fluidic device of any of the preceding paragraphs, wherein an inlet port and an outlet port are on a same side of the closed chamber such that a peripheral flow is established for any given fluid of two fluids, each of the fluids corresponding to an inlet port/outlet port pair.

53. The controlled fluidic device of any of the preceding paragraphs, wherein the gradient established is a concentration gradient.

54. The controlled fluidic device of any of the preceding paragraphs, wherein the gradient established is a temperature gradient.

55. The controlled fluidic device of any of the preceding paragraphs, wherein the closed chamber comprises a space therein and a gel medium in said space.

56. The controlled fluidic device of paragraph 55, wherein the different gel-types include one of collagen, agar, and mucin.

57. The controlled fluidic device of paragraph 2, wherein the wells have a depth of approximately 5 µm to 100 µm.

58. The controlled fluidic device of paragraph 2, wherein the wells have a depth of approximately 25 µm to 30 µm for bacterial cells.

59. The controlled fluidic device of paragraph 2, wherein the wells have a depth of approximately 50 µm to 100 µm for mammalian cells.

60. The controlled fluidic device of any one of the preceding paragraphs, wherein the device is formed by 3D printing.

61. The controlled fluidic device of any one of the preceding paragraphs, wherein the device is formed of silica based material.

62. A method of identifying altered chemical resistance in a bacterial population in the controlled fluidic device of paragraph 0, the method comprising:
   (a) synthesizing a mutant bacterial strain to express fluorescent proteins;
   (b) introducing a known concentration of the bacterial strain into the closed chamber;
   (c) administering the two or more different fluids into the closed chamber via the two more inlet ports;
   (d) isolating DNA from a single cell;
   (d) purifying DNA from bacteria;
   (e) sequencing DNA from bacteria;
   (f) preparing and sequencing a single composite sequence library;
   wherein identification of alteration in level of expression compared to a baseline gene expression measurement of at least one biomarker is indicative of chemical resistance, and
   wherein the baseline gene expression measurement is the gene expression measured in the microfluidic well prior to administration of the two or more different fluids.

63. A method of evaluating response in a cell population in the controlled fluidic device of paragraph 0, the method comprising:
   (a) introducing a cell population into the closed chamber;
   (b) administering the two or more different fluids into the closed chamber via the two more inlet ports such that a concentration gradient is established in the closed chamber; and
   (c) measuring response of the cell population at various concentrations across the concentration gradient.

64. A method of identifying altered bacterial populations according to the preceding paragraph, comprising:
   (a) a microfluidic device having a closed chamber having an upper surface and a lower surface and a peripheral plate edge having a predetermined depth;
   (b) a plurality of microfluidic wells extending from the upper surface of the closed chamber, each well connected to adjacent ones of the plurality of wells by microchannels extending from the upper surface of the plate and extending from a first well to a second well such that the first well is in fluid communication with the second well;
   wherein the microfluidic device and plurality of wells connected by microchannels creates a chemical concentration gradient in adjacent microfluidic wells wherein one microfluidic well has a different chemical concentration than an adjacent microfluidic well;
   (c) providing a chemical dye via an inlet port of the closed chamber;
   (d) providing a chemical via an inlet port of the closed chamber, wherein a first inlet provides a diluent and a second inlet provides a chemical of interest;
   (e) optionally providing a second chemical via an inlet port of the closed chamber;
   (f) an outlet port of the closed chamber; and
   (g) a peripheral flow channel adjacent to a portion of the peripheral plate edge and extending from the inlet port to the outlet port.

65. The method according to paragraphs 62 or 64, wherein the measurement of gene expression is made by detecting the quantity of RNA transcribed by the biomarker.

66. The method of paragraphs 62 or 64, wherein the measurement of gene expression is made by detecting the quantity of DNA produced from reverse transcription of an RNA transcribed by the biomarker.

67. The method of paragraphs 62 or 64, wherein the measurement of gene expression is made by detecting a polypeptide or protein encoded by the biomarker.

68. The method of paragraphs 62 or 64, wherein at least one biomarker is operably linked to a fluorescent protein.

69. A method of identifying a pharmacophore associated with an altered bacterial population according to any one of paragraphs 62 to 68 wherein the altered bacterial population is produced in an altered level of gene expression compared to a baseline gene expression.

70. A method of identifying a compound associated with an altered bacterial population according to any one of paragraphs 62 to 68, comprising:
   (a) designing a combinatorial library wherein each member of the library comprises at least one pharmacophore associated with the altered gene expression,
   wherein alteration in level of expression compared to a baseline gene expression measurement of at least one biomarker is indicative of an altered bacterial population,
   (b) synthesizing a plurality of compounds from said combinatorial library; and,
   (c) screening said compounds for candidates associated with the altered bacterial population.

71. The method of any one of paragraphs 64 to 68, wherein the closed chamber is a polygonal plate.

72. The method of any one of paragraphs 64 to 68, wherein the microfluidic wells have a polygonal cross section in a plane parallel to the lower surface of the closed chamber, each well having a plurality of vertices, wherein the microchannels extending from the first well to the second well extend from a vertex of the polygonal cross section of the first well to a vertex of the polygonal cross section of the second well.

73. The method of any of paragraphs 64 to 72, wherein the peripheral flow channel is defined by laminar flow of at least one of the fluids in the closed chamber.

74. An array of controlled fluidic devices, comprising a plurality of controlled microfluidic devices according to paragraph 0.

All publications, patents, and patent applications mentioned herein are incorporated by reference to the same extent as if each individual publication, patent or patent application was specifically and individually indicated to be incorporated by reference in its entirety.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

What is claimed is:

1. A microfluidic device component for establishing a gradient, comprising:
   a chamber defining an interior space; and
   two or more inlet ports that deliver two or more different fluids to the interior space of the chamber and two or more outlet ports, wherein the two or more inlet ports comprise at least a first inlet port and a second inlet port, the two or more outlet ports comprise at least a first outlet port and a second outlet port, the first inlet port and the first outlet port are located at a first vertex of the chamber and the second inlet port and second outlet port are located at a second opposing vertex of the chamber so that the flow of the two or more fluids into the interior space results in formation of a gradient across the interior space; wherein the interior space comprises a plurality of three or more regularly spaced columns throughout the interior space and a plurality of three or more wells interspersed between the plurality of columns and wherein each well is in fluid communication with adjacent wells.

2. The microfluidic device component of claim 1, wherein the chamber is polygonal in shape.

3. The microfluidic device component of claim 2, wherein the chamber is square or hexagonal in shape.

4. The microfluidic device component of claim 1, wherein the chamber is 1.4 mm to 1.7 mm wide.

5. The microfluidic device component of claim 1, wherein the two or more inlet ports and the two or more outlet ports are connected via peripheral channels running along an exterior edge of the chamber, and wherein the peripheral channels comprise a plurality of openings along an interior wall of the chamber to allow fluid communication between the peripheral channels and the interior space.

6. The microfluidic device component of claim 5, wherein the peripheral flow channels have a depth of approximately 5 μm to 500 μm.

7. The microfluidic device component of claim 1, wherein the first inlet port and first outlet port are separated by an angle of 130 to 220 degrees and the second inlet port and second outlet port are separated by an angle of 130 to 220 degrees.

8. A method for screening one or more cell types for one or more biological functions, comprising:
   introducing one or more cell types into the chamber of the microfluidic device component of claim 1;
   flowing two or more solutions into the chamber to establish a gradient within the interior space of the chamber; and
   measuring a cellular response of the one or more cell types across the gradient.

9. The method of claim 8, wherein measuring the cellular response comprises detecting changes in cell membrane morphologies, changes in nuclear or organelle morphologies, changes in cytoskeletal arrangement, changes in vesicle trafficking, changes in cell motility, cell inhibition, cell death, neoplastic transformation or a combination thereof.

10. The method of claim 8, wherein measuring the cellular response comprises detecting a label or other detectable signals generated by a reporter element.

11. The method of claim 10, wherein the label is detectable by photochemical, biochemical, spectroscopic, immunochemical, electrical, optical or chemical detection.

12. The method of claim 11, where measuring the cellular response comprises light and/or fluorescent microscopy imaging of one or more wells in the interior space of the chamber.

13. The method of claim 8, wherein the two or more solutions comprise a test solution and a diluent.

14. The method of claim 13, wherein the test solution comprises one or more therapeutic agents.

15. The method of claim 13, wherein the cell types are one or more bacterial cells and the test solution comprises one or more antibiotics.

16. The method of claim 8, further comprising isolating cells from one or more wells in the interior space of the chamber.

17. The method of claim 16, further comprising sequencing of the isolated cells.

18. A method for identifying an agent that inhibits cellular growth and/or viability of tumorigenic or transformed cells, comprising:
   introducing cells from a sample into the chamber of the microfluidic device component of claim 1;
   culturing the cells in low or no attachment conditions and in the presence of a test agent; and
   detecting inhibition of cell growth or viability.

19. The method of claim 18, wherein the sample is a patient sample.

20. The method of claim 19, wherein the patient sample is from a tumor.

21. The method of claim 18, wherein the test agent is a drug or biological therapeutic.

* * * * *

UNITED STATES PATENT AND TRADEMARK OFFICE
CERTIFICATE OF CORRECTION

PATENT NO. : 11,904,310 B2
APPLICATION NO. : 15/772035
DATED : February 20, 2024
INVENTOR(S) : Anindita Basu et al.

It is certified that error appears in the above-identified patent and that said Letters Patent is hereby corrected as shown below:

On the Title Page

On the page 4, in Column 1, item (56) under "Other Publications", Line 26, delete "filed" and insert -- filed on --.

In the Specification

In Column 12, Line 1, delete "1015" and insert -- $10^{15}$ --.

In Column 13, Line 65, delete "1011" and insert -- $10^{11}$ --.

In Column 13, Line 66, delete "1015" and insert -- $10^{15}$ --.

Signed and Sealed this
Twenty-ninth Day of October, 2024

Katherine Kelly Vidal
*Director of the United States Patent and Trademark Office*